US006361939B1

(12) United States Patent
Bates et al.

(10) Patent No.: US 6,361,939 B1
(45) Date of Patent: *Mar. 26, 2002

(54) ISOLATED MAMMALIAN DENDRITIC CELL GENES; RELATED REAGENTS

(75) Inventors: Elizabeth Esther Mary Bates; Blandine Marie de Saint-Vis; Christophe Caux, all of Lyons; Serge J. E. Lebecque, Civrieux d'Azergue, all of (FR); Jacques Banchereau, Dallas, TX (US)

(73) Assignee: Schering Corporation, Kenilworth, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,289

(22) Filed: Nov. 25, 1997

Related U.S. Application Data

(60) Provisional application No. 60/031,806, filed on Nov. 27, 1996, and provisional application No. 60/032,767, filed on Dec. 11, 1996.

(51) Int. Cl.[7] .......................... C07H 21/04; C12N 1/20; C12P 21/06; C12Q 1/68
(52) U.S. Cl. .................... 435/6; 435/69.1; 435/252.33; 435/320.1; 435/325; 435/366; 435/975; 530/350; 536/23.5
(58) Field of Search .......................... 435/366, 252.33, 435/97.5, 6, 69.1, 320.1, 325; 530/380; 536/23.5

(56) References Cited

U.S. PATENT DOCUMENTS 5,646,251 A    7/1997   Ruegg et al.

FOREIGN PATENT DOCUMENTS

| WO | WO 93/21318 | 10/1993 |
| WO | WO 95/29236 | 11/1995 |
| WO | WO 96 34880 | 11/1996 |

OTHER PUBLICATIONS

Darnell, et al. Molecular Cell Biology, Scientific American Books, W.H. Freeman and Company, New York, NY, p. 255, 1986.*

Wintero, et al., Evaluation and characterization of a porcine small intestine cDNA library: analysis of 839 clones. Mamm. Genome 7:509–517, Aug. 2, 1996.*

Hillier, L., et al., GenBank Accesiion No. N49642, Feb. 14, 1996.*

Elizabeth E.M. Bates, et al., *Eur. J. Immunol.*, 27:2471–2477, 1997. "Identification and analysis of a a novel member of the ubiquitin family expressed in dendritic cells and mature B cells".

Michael Cardone and Keith Mostov, *FEBS Letters*, 376:74–76, Oct. 1995. "Wortmannin inhibits transcytosis of dimeric IgA by the polymeric immunoglobulin receptor".

Meltsje de Hoop, et al., *J. Cell. Biology*, 130(6):1447–1459, Sep. 1995. "Intracellular Routing of Wild–Type and Mated Polymeric Immunolglobulin Receptor in Hippocampal Neurons in Culture".

Thomas Ferkol, et al., *J. Clin. Investigation*, 95:493–502, Feb. 1995. "Gene Transfer into the Airway Epithelium of Animals by Targeting the Polymeric Immunoglobulin Receptor".

M. Fukuda, et al., *Gen Bank*, Accession No. J04182, Jan. 11, 1995. "Cloning of cDNAs encoding human lysomal membrane glycoproteins, h–lamp–1 and h–lamp–2. Comparison of their deduced amino acid sequences."

M. Fukuda, et al., *Gen Bank*, Accession No. J04183, Jan. 11, 1995, "Cloning of cDNAs encoding human lysomal membrane glycoproteins, h–lamp–1 and h–lamp–2. Comparison of their deduced amino acid sequences."

Jeffrey R. Gruen, et al., *Blood*, 90(11):4252–4265, Dec. 1, 1997. "Evolving Views of the Major Histocompatibility Complex".

Arthur L. Haas, et al., *The Journal of Biological Chemistry*, 262(23):11315–11323, 1987. "Interferon Induces a 15–Kilodalton Protein Exhibiting Marked Homology to Ubiquitin".

Keith R. Loeb and Arthur L. Haas, *J. Bio. Chem.*, 267(11):7806–7813, Apr. 1992. "The Interferon–inducible 15–kDa Ubiquitin Homolog Conjugates to Intracellular Proteins".

Keith R. Loeb and Arthur L. Haas, *Mol. Cell. Biol.*, 14(12):8408–8419, Dec. 1994. "Conjugates of Ubiquitin Cross–Reactive Protein Distribute in a Cytoskeletal Pattern".

Lowe, et al., *Journal of Pathology*, 177:163–169, 1995. "Immunohistochemical Localization of Ubiquitin Cross–Reactive Protein in Human Tissues".

Mary B. Mazanec, et al., *J. Virology*, 69:1339–1343, Feb. 1995. "Intracellular Neutralization of Influenza Virus by Immunoglobulin A Anti–Hemagglutinin Monoclonal Antibodies".

Linde Meyaard, et al., *Immunity*, 7:283–290, Aug. 1997. "LAIR–1, a Novel Inhibitory Receptor Expressed on Human Mononuclear Leukocytes".

(List continued on next page.)

Primary Examiner—David Saunders
Assistant Examiner—Mary Beth Tung
(74) Attorney, Agent, or Firm—Edwin P. Ching; Jaye P. McLaughlin

(57) ABSTRACT

Polynucleotides encoding various dendritic cell specific proteins from a primate are provided. Uses of purified sequences are also disclosed, including producing related reagents, e.g., specific antibodies, and purified proteins. Methods of using these reagents and related diagnostic kits are also described.

16 Claims, No Drawings

OTHER PUBLICATIONS

Brett P. Monia, et al., *Bio/Technology*, 8:209–215, Mar. 1990. "New Perspectives on the Structure and Function of Ubiquitin".

Morihiko Nakamura, et al., *Journal of Immunology*, 156:532–538, 1996. "Ubiquitin–Like Moiety of the Monoclonal Nonspecific Suppressor Factorβ Is Responsible for Its Activity".

Jana Narasimhan, et al., *J. Biol. Chem.*, 271(1):324–330, Jan. 1996. "Conjugation of the 15kDa Interferon–induced Ubiquitin Homolog Is Distinct from that of Ubiquitin".

Stienman, *Annual Review of Immunology*, 9:271–296, 1991. "The Dendritic Cell System and Its Role in Immunogenicity".

Daniela Toniolo, et al., *Proc. Natl. Acad. Sci., USA*, 85:851–855, Feb. 1988. "A "housekeeping" gene on the X chromosome encodes a protein similar to ubiquitin".

S. Uthayakumar, et al., *Gen Bank*, Accession No. J04183, Jan. 11, 1995. "Cell surface accumulation of overexpressed hamster lysosomal membrane glycoproteins".

Morihiko Nakamura, et al., *PNAS*, 92:3463–3467, Apr. 1995. "Molecular cloning and characterization of a cDNA encoding monoclonal nonspecific supressor factor".

David G. Jackson, et al., *Eur. J. Immunol.*, 22:1157–1163, 1992. "Molecular cloning of a novel member of the immunoglobulin gene superfamily homologous to the polymeric immunoglobulin receptor".

L. Hillier, et al., *Gen Bank*, Accession No. N49642, Feb. 18, 1996. "H. sapiens clone 243789, ubiquitin precursor".

M. Marra, et al., *Gen Bank*, Accession No. AA119390, Nov. 21, 1996. "Mus musculus cDNA clone 573650".

* cited by examiner

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 777 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 19..513

(xi) SEQUENCE DESCRIPTION: SEQ ID NO:1:

```
GGCCCCTTGT CTGCAGAG ATG GCT CCC AAT GCT TCC TGC CTC TGT GTG CAT        51
                    Met Ala Pro Asn Ala Ser Cys Leu Cys Val His
                     1               5                  10

GTC CGT TCC GAG GAA TGG GAT TTA ATG ACC TTT GAT GCC AAC CCA TAT        99
Val Arg Ser Glu Glu Trp Asp Leu Met Thr Phe Asp Ala Asn Pro Tyr
             15                  20                  25

GAC AGC GTG AAA AAA ATC AAA GAA CAT GTC CGG TCT AAG ACC AAG GTT       147
Asp Ser Val Lys Lys Ile Lys Glu His Val Arg Ser Lys Thr Lys Val
         30                  35                  40

CCT GTG CAG GAC CAG GTT CTT TTG CTG GGC TCC AAG ATC TTA AAG CCA       195
Pro Val Gln Asp Gln Val Leu Leu Leu Gly Ser Lys Ile Leu Lys Pro
     45                  50                  55

CGG AGA AGC CTC TCA TCT TAT GGC ATT GAC AAA GAG AAG ACC ATC CAC       243
Arg Arg Ser Leu Ser Ser Tyr Gly Ile Asp Lys Glu Lys Thr Ile His
 60                  65                  70                  75

CTT ACC CTG AAA GTG GTG AAG CCC AGT GAT GAG GAG CTG CCC TTG TTT       291
Leu Thr Leu Lys Val Val Lys Pro Ser Asp Glu Glu Leu Pro Leu Phe
                 80                  85                  90

CTT GTG GAG TCA GGT GAT GAG GCA AAG AGG CAC CTC CTC CAG GTG CGA       339
Leu Val Glu Ser Gly Asp Glu Ala Lys Arg His Leu Leu Gln Val Arg
             95                 100                 105

AGG TCC AGC TCA GTG GCA CAA GTG AAA GCA ATG ATC GAG ACT AAG ACG       387
Arg Ser Ser Ser Val Ala Gln Val Lys Ala Met Ile Glu Thr Lys Thr
        110                 115                 120

GGT ATA ATC CCT GAG ACC CAG ATT GTG ACT TGC AAT GGA AAG AGA CTG       435
Gly Ile Ile Pro Glu Thr Gln Ile Val Thr Cys Asn Gly Lys Arg Leu
    125                 130                 135
```

```
GAA GAT GGG AAG ATG ATG GCA GAT TAC GGC ATC AGA AAG GGC AAC TTA      483
Glu Asp Gly Lys Met Met Ala Asp Tyr Gly Ile Arg Lys Gly Asn Leu
140                 145                 150                 155

CTC TTC CTG GCA TCT TAT TGT ATT GGA GGG TGACCACCCT GGGGATGGGG        533
Leu Phe Leu Ala Ser Tyr Cys Ile Gly Gly
                160                 165

TGTTGGCAGG GGTCAAAAAG CTTATTTCTT TTAATCTCTT ACTCAACGAA CACATCTTCT    593

GATGATTTCC CAAAATTAAT GAGAATGAGA TGAGTAGAGT AAGATTTGGG TGGGATGGGT    653

AGGATGAAGT ATATTGCCCA ACTCTATGTT TCTTTGATTC TAACACAATT AATTAAGTGA    713

CATGATTTTT ACTAATGTAT TACTGAGACT AGTAAATAAA TTTTTAAGGC AAAATAGAGC    773

ATTC                                                                 777
```

(2) INFORMATION FOR SEQ ID NO:2:

(i) SEQUENCE CHARACTERISTICS:
        (A) LENGTH: 165 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Pro Asn Ala Ser Cys Leu Cys Val His Val Arg Ser Glu Glu
 1               5                  10                  15

Trp Asp Leu Met Thr Phe Asp Ala Asn Pro Tyr Asp Ser Val Lys Lys
                20                  25                  30

Ile Lys Glu His Val Arg Ser Lys Thr Lys Val Pro Val Gln Asp Gln
            35                  40                  45

Val Leu Leu Gly Ser Lys Ile Leu Lys Pro Arg Arg Ser Leu Ser
        50                  55                  60

Ser Tyr Gly Ile Asp Lys Glu Lys Thr Ile His Leu Thr Leu Lys Val
65                  70                  75                  80

Val Lys Pro Ser Asp Glu Glu Leu Pro Leu Phe Leu Val Glu Ser Gly
                85                  90                  95

Asp Glu Ala Lys Arg His Leu Leu Gln Val Arg Arg Ser Ser Ser Val
                100                 105                 110

Ala Gln Val Lys Ala Met Ile Glu Thr Lys Thr Gly Ile Ile Pro Glu
            115                 120                 125

Thr Gln Ile Val Thr Cys Asn Gly Lys Arg Leu Glu Asp Gly Lys Met
        130                 135                 140

Met Ala Asp Tyr Gly Ile Arg Lys Gly Asn Leu Leu Phe Leu Ala Ser
145                 150                 155                 160

Tyr Cys Ile Gly Gly
                165
```

(2) INFORMATION FOR SEQ ID NO:3:

(i) SEQUENCE CHARACTERISTICS:
        (A) LENGTH: 496 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 8..493

(xi) SEQUENCE DESCRIPTION: SEQ ID NO:3:

```
TACAGAC ATG GCT TCT GTC CGC ACC TGT GTT GTC CGT TCA GAC CAA TGG        49
        Met Ala Ser Val Arg Thr Cys Val Val Arg Ser Asp Gln Trp
        1               5                   10

CGG TTA ATG ACC TTT GAG ACC ACT GAG AAT GAC AAA GTG AAG AAG ATA         97
Arg Leu Met Thr Phe Glu Thr Thr Glu Asn Asp Lys Val Lys Lys Ile
15              20                  25                  30

AAT GAA CAT ATT AGG TCC CAA ACC AAG GTC TCT GTA CAG GAC CAG ATC        145
Asn Glu His Ile Arg Ser Gln Thr Lys Val Ser Val Gln Asp Gln Ile
                35                  40                  45

CTT CTG CTA GAC TCC AAA ATC CTC AAG CCC CAT CGA AAA TTG TCA TCC        193
Leu Leu Leu Asp Ser Lys Ile Leu Lys Pro His Arg Lys Leu Ser Ser
            50                  55                  60

TAT GGG ATT GAC AAG GAA ACC ACT ATC CAC CTT ACC CTG AAG GTG GTG        241
Tyr Gly Ile Asp Lys Glu Thr Thr Ile His Leu Thr Leu Lys Val Val
        65                  70                  75

AAG CCC AGT GAT GAA GAG CTG CCC TTG TTT CTG GTG GAG TCC AAA AAC        289
Lys Pro Ser Asp Glu Glu Leu Pro Leu Phe Leu Val Glu Ser Lys Asn
80              85                  90

GAG GGG CAA AGG CAC CTC CTC CGA GTT CGA AGA TCC AGC TCA GTG GCC        337
Glu Gly Gln Arg His Leu Leu Arg Val Arg Arg Ser Ser Ser Val Ala
95              100                 105                 110

CAG GTG AAA GAG ATG ATC GAG AGT GTG ACC TCT GTG ATC CCT AAG AAG        385
Gln Val Lys Glu Met Ile Glu Ser Val Thr Ser Val Ile Pro Lys Lys
                115                 120                 125

CAG GTT GTG AAT TGC AAC GGA AAG AAG CTG GAA GAT GGA AAG ATC ATG        433
Gln Val Val Asn Cys Asn Gly Lys Lys Leu Glu Asp Gly Lys Ile Met
            130                 135                 140

GCT GAC TAC AAC ATC AAG AGT GGC AGT TTG CTC TTT CTG ACA ACA CAC        481
Ala Asp Tyr Asn Ile Lys Ser Gly Ser Leu Leu Phe Leu Thr Thr His
        145                 150                 155

TGC ACT GGG GGA TGA                                                    496
Cys Thr Gly Gly
160
```

(2) INFORMATION FOR SEQ ID NO:4:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser Val Arg Thr Cys Val Val Arg Ser Asp Gln Trp Arg Leu
1               5                   10                  15

Met Thr Phe Glu Thr Thr Glu Asn Asp Lys Val Lys Lys Ile Asn Glu
                20                  25                  30

His Ile Arg Ser Gln Thr Lys Val Ser Val Gln Asp Gln Ile Leu Leu
            35                  40                  45

Leu Asp Ser Lys Ile Leu Lys Pro His Arg Lys Leu Ser Ser Tyr Gly
        50                  55                  60

Ile Asp Lys Glu Thr Thr Ile His Leu Thr Leu Lys Val Val Lys Pro
65                  70                  75                  80

Ser Asp Glu Glu Leu Pro Leu Phe Leu Val Glu Ser Lys Asn Glu Gly
                85                  90                  95

Gln Arg His Leu Leu Arg Val Arg Ser Ser Ser Val Ala Gln Val
            100                 105                 110
```

```
Lys Glu Met Ile Glu Ser Val Thr Ser Val Ile Pro Lys Lys Gln Val
        115                 120                 125

Val Asn Cys Asn Gly Lys Lys Leu Glu Asp Gly Lys Ile Met Ala Asp
130                 135                 140

Tyr Asn Ile Lys Ser Gly Ser Leu Leu Phe Leu Thr Thr His Cys Thr
145                 150                 155                 160

Gly Gly
```

(2) INFORMATION FOR SEQ ID NO:5:

(i) SEQUENCE CHARACTERISTICS:
        (A) LENGTH: 1040 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 45..767

(ix) FEATURE:
        (A) NAME/KEY: mat_peptide
        (B) LOCATION: 111..767

(xi) SEQUENCE DESCRIPTION: SEQ ID NO:5:

```
TTCCTTTCAA ATACACACCC CAACCCGCCC CGGCATACAC AGAA ATG GGG ACT GCG          56
                                                 Met Gly Thr Ala
                                                 -22     -20

AGC AGA AGC AAC ATC GCT CGC CAT CTG CAA ACC AAT CTC ATT CTA TTT          104
Ser Arg Ser Asn Ile Ala Arg His Leu Gln Thr Asn Leu Ile Leu Phe
        -15                 -10                  -5

TGT GTC GGT GCT GTG GGC GCC TGT ACT CTC TCT GTC ACA CAA CCG TGG          152
Cys Val Gly Ala Val Gly Ala Cys Thr Leu Ser Val Thr Gln Pro Trp
         1                   5                  10

TAC CTA GAA GTG GAC TAC ACT CAT GAG GCC GTC ACC ATA AAG TGT ACC          200
Tyr Leu Glu Val Asp Tyr Thr His Glu Ala Val Thr Ile Lys Cys Thr
 15                 20                  25                  30

TTC TCC GCA ACC GGA TGC CCT TCT GAG CAA CCA ACA TGC CTG TGG TTT          248
Phe Ser Ala Thr Gly Cys Pro Ser Glu Gln Pro Thr Cys Leu Trp Phe
             35                  40                  45

CGC TAC GGT GCT CAC CAG CCT GAG AAC CTG TGC TTG GAC GGG TGC AAA          296
Arg Tyr Gly Ala His Gln Pro Glu Asn Leu Cys Leu Asp Gly Cys Lys
                 50                  55                  60

AGT GAG GCA GAC AAG TTC ACA GTG AGG GAG GCC CTC AAA GAA AAC CAA          344
Ser Glu Ala Asp Lys Phe Thr Val Arg Glu Ala Leu Lys Glu Asn Gln
             65                  70                  75

GTT TCC CTC ACT GTA AAC AGA GTG ACT TCA AAT GAC AGT GCA ATT TAC          392
Val Ser Leu Thr Val Asn Arg Val Thr Ser Asn Asp Ser Ala Ile Tyr
 80                  85                  90

ATC TGT GGA ATA GCA TTC CCC AGT GTG CCG GAA GCG AGA GCT AAA CAG          440
Ile Cys Gly Ile Ala Phe Pro Ser Val Pro Glu Ala Arg Ala Lys Gln
 95                 100                 105                 110

ACA GGA GGA GGG ACC ACA CTG GTG GTA AGA GAA ATT AAG CTG CTC AGC          488
Thr Gly Gly Gly Thr Thr Leu Val Val Arg Glu Ile Lys Leu Leu Ser
                115                 120                 125

AAG GAA CTG CGG AGC TTC CTG ACA GCT CTT GTA TCA CTG CTC TCT GTC          536
Lys Glu Leu Arg Ser Phe Leu Thr Ala Leu Val Ser Leu Leu Ser Val
            130                 135                 140

TAT GTG ACC GGT GTG TGC GTG GCC TTC ATA CTC CTC TCC AAA TCA AAA          584
Tyr Val Thr Gly Val Cys Val Ala Phe Ile Leu Leu Ser Lys Ser Lys
                145                 150                 155
```

```
TCC AAC CCT CTA AGA AAG AAA GAA ATA AAA GAA GAC TCA CAA AAG AAG        632
Ser Asn Pro Leu Arg Lys Lys Glu Ile Lys Glu Asp Ser Gln Lys Lys
        160                 165                 170

AAG AGT GCT CGG CGT ATT TTT CAG GAA ATT GCT CAA GAA CTA TAC CAT        680
Lys Ser Ala Arg Arg Ile Phe Gln Glu Ile Ala Gln Glu Leu Tyr His
175                 180                 185                 190

AAG AGA CAT GTG AAA ACA AAT CAG CAA TCT GAG AAA GAT AAC AAC ACT        728
Lys Arg His Val Glu Thr Asn Gln Gln Ser Glu Lys Asp Asn Asn Thr
                    195                 200                 205

TAT GAA AAC AGA AGA GTA CTT TCC AAC TAT GAA AGG CCA TAGAAACGTT         777
Tyr Glu Asn Arg Arg Val Leu Ser Asn Tyr Glu Arg Pro
        210                 215

TTAATTTTCA ATGAAGTCAC TGAAAATCCA ACTCCAGGAG CTATGGCAGT GTTAATGAAC      837

ATATATCATC AGGTCTTAAA AAAAAAATAA AGGTAAACTG AAAAGACAAC TGGCTACAAA      897

GAAGGATGTC AGAATGTAAG GAAACTATAA CTAAATAGTCA TTACCAAAAT ACTAAAACCC     957

AACAAAATGC AACTGAAAAA TACCTTCCAA ATTTGCCAAG AAAAAAAATT CTATTAAACT     1017

AAAAAAAAAA AAAAAAAAAA AAA                                            1040
```

(2) INFORMATION FOR SEQ ID NO:6:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Thr Ala Ser Arg Ser Asn Ile Ala Arg His Leu Gln Thr Asn
-22         -20                 -15                 -10

Leu Ile Leu Phe Cys Val Gly Ala Val Gly Ala Cys Thr Leu Ser Val
        -5                  1                   5                  10

Thr Gln Pro Trp Tyr Leu Glu Val Asp Tyr Thr His Glu Ala Val Thr
                    15                  20                  25

Ile Lys Cys Thr Phe Ser Ala Thr Gly Cys Pro Ser Glu Gln Pro Thr
                30                  35                  40

Cys Leu Trp Phe Arg Tyr Gly Ala His Gln Pro Glu Asn Leu Cys Leu
        45                  50                  55

Asp Gly Cys Lys Ser Glu Ala Asp Lys Phe Thr Val Arg Glu Ala Leu
60                  65                  70

Lys Glu Asn Gln Val Ser Leu Thr Val Asn Arg Val Thr Ser Asn Asp
75                  80                  85                  90

Ser Ala Ile Tyr Ile Cys Gly Ile Ala Phe Pro Ser Val Pro Glu Ala
                95                  100                 105

Arg Ala Lys Gln Thr Gly Gly Gly Thr Thr Leu Val Val Arg Glu Ile
            110                 115                 120

Lys Leu Leu Ser Lys Glu Leu Arg Ser Phe Leu Thr Ala Leu Val Ser
        125                 130                 135

Leu Leu Ser Val Tyr Val Thr Gly Val Cys Val Ala Phe Ile Leu Leu
        140                 145                 150

Ser Lys Ser Lys Ser Asn Pro Leu Arg Lys Lys Glu Ile Lys Glu Asp
155                 160                 165                 170

Ser Gln Lys Lys Ser Ala Arg Arg Ile Phe Gln Glu Ile Ala Gln
                175                 180                 185

Glu Leu Tyr His Lys Arg His Val Glu Thr Asn Gln Gln Ser Glu Lys
            190                 195                 200
```

```
                    Asp Asn Asn Thr Tyr Glu Asn Arg Arg Val Leu Ser Asn Tyr Glu Arg
                            205                 210                 215

Pro (2) INFORMATION FOR SEQ ID NO:7:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 45..767

(ix) FEATURE:
        (A) NAME/KEY: mat_peptide
        (B) LOCATION: 111..767

(ix) FEATURE:
        (A) NAME/KEY: misc_feature
        (B) LOCATION: 1013
        (D) OTHER INFORMATION: /note= "nucleotides 1013 and 1014 are
            designated C, but may be C or T"

(xi) SEQUENCE DESCRIPTION: SEQ ID NO:7:

TTCCTTTCAA ATACACACCC CAACCCGCCC CGGCATACAC AGAA ATG GGG ACT GCG           56
                                                 Met Gly Thr Ala
                                                 -22     -20

AGC AGA AGC AAC ATC GCT CGC CAT CTG CAA ACC AAT CTC ATT CTA TTT          104
Ser Arg Ser Asn Ile Ala Arg His Leu Gln Thr Asn Leu Ile Leu Phe
        -15                 -10                  -5

TGT GTC GGT GCT GTG GGC GCC TGT ACT CTC TCT GTC ACA CAA CCG TGG          152
Cys Val Gly Ala Val Gly Ala Cys Thr Leu Ser Val Thr Gln Pro Trp
            1               5                  10

TAC CTA GAA GTG GAC TAC ACT CAT GAG GCC GTC ACC ATA AAG TGT ACC          200
Tyr Leu Glu Val Asp Tyr Thr His Glu Ala Val Thr Ile Lys Cys Thr
 15              20                  25                  30

TTC TCC GCA ACC GGA TGC CCT TCT GAG CAA CCA ACA TGC CTG TGG TTT          248
Phe Ser Ala Thr Gly Cys Pro Ser Glu Gln Pro Thr Cys Leu Trp Phe
             35                  40                  45

CGC TAC GGT GCT CAC CAG CCT GAG AAC CTG TGC TTG GAC GGG TGC AAA          296
Arg Tyr Gly Ala His Gln Pro Glu Asn Leu Cys Leu Asp Gly Cys Lys
                 50                  55                  60

AGT GAG GCA GAC AAG TTC ACA GTG AGG GAG GCC CTC AAA GAA AAC CAA          344
Ser Glu Ala Asp Lys Phe Thr Val Arg Glu Ala Leu Lys Glu Asn Gln
             65                  70                  75

GTT TCC CTC ACT GTA AAC AGA GTG ACT TCA AAT GAC AGT GCA ATT TAC          392
Val Ser Leu Thr Val Asn Arg Val Thr Ser Asn Asp Ser Ala Ile Tyr
         80                  85                  90

ATC TGT GGA ATA GCA TTC CCC AGT GTG CCG GAA GCG AGA GCT AAA CAG          440
Ile Cys Gly Ile Ala Phe Pro Ser Val Pro Glu Ala Arg Ala Lys Gln
 95                 100                 105                 110

ACA GGA GGA GGG ACC ACA CTG GTG GTA AGA GAA ATT AAG CTG CTC AGC          488
Thr Gly Gly Gly Thr Thr Leu Val Val Arg Glu Ile Lys Leu Leu Ser
                 115                 120                 125

AAG GAA CTG CGG AGC TTC CTG ACA GCT CTT GTA TCA CTG CTC TCT GTC          536
Lys Glu Leu Arg Ser Phe Leu Thr Ala Leu Val Ser Leu Leu Ser Val
             130                 135                 140

TAT GTG ACC GGT GTG TGC GTG GCC TTC ATA CTC CTC TCC AAA TCA AAA          584
Tyr Val Thr Gly Val Cys Val Ala Phe Ile Leu Leu Ser Lys Ser Lys
         145                 150                 155
```

-continued

```
TCC AAC CCT CTA AGA AAG AAA GAA ATA AAA GAA GAC TCA CAA AAG AAG    632
Ser Asn Pro Leu Arg Lys Lys Glu Ile Lys Glu Asp Ser Gln Lys Lys
    160                 165                 170

AAG AGT GCT CGG CGT ATT TTT CAG GAA ATT GCT CAA GAA CTA TAC CAT    680
Lys Ser Ala Arg Arg Ile Phe Gln Glu Ile Ala Gln Glu Leu Tyr His
175                 180                 185                 190

AAG AGA CAT GTG GAA ACA AAT CAG CAA TCT GAG AAA GAT AAC AAC ACT    728
Lys Arg His Val Glu Thr Asn Gln Gln Ser Glu Lys Asp Asn Asn Thr
                195                 200                 205

TAT GAA AAC AGA AGA GTA CTT TCC AAC TAT GAA AGG CCA TAGAAACGTT     777
Tyr Glu Asn Arg Arg Val Leu Ser Asn Tyr Glu Arg Pro
            210                 215

TTAATTTTCA ATGAAGTCAC TGAAAATCCA ACTCCAGGAG CTATGGCAGT GTTAATGAAC  837

ATATATCATC AGGTCTTAAA AAAAAAATAA AGGTAAACTG AAAAGACAAC TGGCTACAAA  897

GAAGGATGTC AGAATGTAAG GAAACTATAA CTAAATAGTCA TTACCAAAAT ACTAAAACCC 957

AACAAAATGC AACTGAAAAA TACCTTCCAA ATTTGCCAAG AAAAAAAATT CTATTCCAAA  1017

CTAAAAAAAA AAAAAAAAAA AAAAA                                       1042
```

(2) INFORMATION FOR SEQ ID NO:8:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Thr Ala Ser Arg Ser Asn Ile Ala Arg His Leu Gln Thr Asn
-22         -20                 -15                 -10

Leu Ile Leu Phe Cys Val Gly Ala Val Gly Ala Cys Thr Leu Ser Val
            -5                  1                   5                   10

Thr Gln Pro Trp Tyr Leu Glu Val Asp Tyr Thr His Glu Ala Val Thr
                15                  20                  25

Ile Lys Cys Thr Phe Ser Ala Thr Gly Cys Pro Ser Glu Gln Pro Thr
                30                  35                  40

Cys Leu Trp Phe Arg Tyr Gly Ala His Gln Pro Glu Asn Leu Cys Leu
            45                  50                  55

Asp Gly Cys Lys Ser Glu Ala Asp Lys Phe Thr Val Arg Glu Ala Leu
60                  65                  70

Lys Glu Asn Gln Val Ser Leu Thr Val Asn Arg Val Thr Ser Asn Asp
75                  80                  85                  90

Ser Ala Ile Tyr Ile Cys Gly Ile Ala Phe Pro Ser Val Pro Glu Ala
                95                  100                 105

Arg Ala Lys Gln Thr Gly Gly Gly Thr Thr Leu Val Val Arg Glu Ile
            110                 115                 120

Lys Leu Leu Ser Lys Glu Leu Arg Ser Phe Leu Thr Ala Leu Val Ser
            125                 130                 135

Leu Leu Ser Val Tyr Val Thr Gly Val Cys Val Ala Phe Ile Leu Leu
            140                 145                 150

Ser Lys Ser Lys Ser Asn Pro Leu Arg Lys Lys Glu Ile Lys Glu Asp
155                 160                 165                 170

Ser Gln Lys Lys Ser Ala Arg Arg Ile Phe Gln Glu Ile Ala Gln
                175                 180                 185

Glu Leu Tyr His Lys Arg His Val Glu Thr Asn Gln Gln Ser Glu Lys
            190                 195                 200
```

```
                                Asp Asn Asn Thr Tyr Glu Asn Arg Arg Val Leu Ser Asn Tyr Glu Arg
                                        205                 210                 215

Pro (2) INFORMATION FOR SEQ ID NO:9:

(i) SEQUENCE CHARACTERISTICS:
        (A) LENGTH: 1253 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 37..750

(ix) FEATURE:
        (A) NAME/KEY: mat_peptide
        (B) LOCATION: 103..750

(xi) SEQUENCE DESCRIPTION: SEQ ID NO:9:

CCACGCGTCC GGGAAAAGGC GGCACATGCA CCAGCG ATG GGC CCT GTG AGC ACG                54
                                        Met Gly Pro Val Ser Thr
                                        -22         -20

AGC AGG AGG GGC CTC CGG CTA GGA ATC AGC CTG ATC CTT CTT CAA GTT               102
Ser Arg Arg Gly Leu Arg Leu Gly Ile Ser Leu Ile Leu Leu Gln Val
    -15                 -10                  -5

GGT GTG GTG GGC GCC TGT ACT GTA TCT GTG CTA CAG CCA GGT TAC CTA               150
Gly Val Val Gly Ala Cys Thr Val Ser Val Leu Gln Pro Gly Tyr Leu
 1               5                  10                  15

GAG GTG GAC TAC ACG TCT CAG ACT GTC ACC ATG GAG TGT ACC TTT TCT               198
Glu Val Asp Tyr Thr Ser Gln Thr Val Thr Met Glu Cys Thr Phe Ser
             20                  25                  30

ACA ACT GGA TGC CCT GCA GTG CAA CCA AAA AGC TTG TGG TTT CGC TGT               246
Thr Thr Gly Cys Pro Ala Val Gln Pro Lys Ser Leu Trp Phe Arg Cys
         35                  40                  45

GGC ACT CAC CAG CCT GAA GCT CTG TGC TTG GAC GGA TGC AGA AAT GAG               294
Gly Thr His Gln Pro Glu Ala Leu Cys Leu Asp Gly Cys Arg Asn Glu
     50                  55                  60

GCA GAC AAG TTC ACA GTG AAA GAA ACC CTG GAC CAG AAC CGA GTC TCC               342
Ala Asp Lys Phe Thr Val Lys Glu Thr Leu Asp Gln Asn Arg Val Ser
 65                  70                  75                  80

CTC ACT GTT AAC AGG CTG TCT CCA AAT GAC AGT GCA ATC TAC ATC TGT               390
Leu Thr Val Asn Arg Leu Ser Pro Asn Asp Ser Ala Ile Tyr Ile Cys
                 85                  90                  95

GGA ATA GCA TTT CCC AAT GAA CCG GTA CCA ACA GCC AAA CAG ACT GGA               438
Gly Ile Ala Phe Pro Asn Glu Pro Val Pro Thr Ala Lys Gln Thr Gly
             100                 105                 110

GAC GGG ACT ACA CTG GTG GTA AGA GAA AGA CTT TTC AGC AGG GAG GTG               486
Asp Gly Thr Thr Leu Val Val Arg Glu Arg Leu Phe Ser Arg Glu Val
         115                 120                 125

CAC AGT CTC CTG ATA GTG CTC TTA GCA CTG CTC GCA GTC TAC GTC ACC               534
His Ser Leu Leu Ile Val Leu Leu Ala Leu Leu Ala Val Tyr Val Thr
     130                 135                 140

GGT GTG TGT GTG ATC TTC ATA GTC CTC TTC AGA TCA AAA TCT AAC ACT               582
Gly Val Cys Val Ile Phe Ile Val Leu Phe Arg Ser Lys Ser Asn Thr
 145                 150                 155                 160

CCA AGA AGC AGA GAA ACC AAG GAA GAC TCG AAA AAG AAG AGT GCT CGA               630
Pro Arg Ser Arg Glu Thr Lys Glu Asp Ser Lys Lys Lys Ser Ala Arg
                 165                 170                 175
```

-continued

```
CGT ATC TTC CAG GAA ATT GCT CAA GAA TTA TAC CAT AAG AGA TAT GTG       678
Arg Ile Phe Gln Glu Ile Ala Gln Glu Leu Tyr His Lys Arg Tyr Val
            180                 185                 190

GAA ACA AGT CAT CAG CCT GAG CAA GAC GGC AAT TAT GAA AAC AGA AAA       726
Glu Thr Ser His Gln Pro Glu Gln Asp Gly Asn Tyr Glu Asn Arg Lys
        195                 200                 205

GCA CTC CCC AGC CCT GGA AGA CCA TAGATGTGCT GACTTTTTAC TTAAACCATT      780
Ala Leu Pro Ser Pro Gly Arg Pro
    210                 215

GACAGTGCAA CTCCAGAATC TATGGCAGTG TGAATGGACA TACAGCAATC CAAACAACAG     840

CAAAGAGAGC TGAGGTGTAG CTTGAGTGGC AAAGTGCTTG CCCAGTAGGC ATGAAGTCTT     900

AGCTTTGATC CTCAGCACCA CATAACTCAG CAAAGTGACA CAAGCCTGTA TTCCCAACAT     960

TGTGTAGTAG TATAAAAAGT CAGAAGTTCA AGGTCATCCC TGACTATAGG ATGAACCTGA    1020

AGTCAGAGAC ATGTTATCTT GTCTCAAAAA CACTGCCACC ACCAAGAGAA AAGGGCAGGA    1080

CAAGTGGGAA ACAGCCAGT CACGCCAGAA GGCAGAGCGG AAGTAACTGT CACGAACCAT     1140

AATGATGGAA TGTGAAAACC TCAAGAAAAC TCAACTGGAG GACCTTTTTT CTAATTTTCC    1200

AGGAACAGTC TAAGGAGCCT CATTTTAAAG AAAAACTTCA CCTTCAGCTT TTA           1253
```

(2) INFORMATION FOR SEQ ID NO:10:

(i) SEQUENCE CHARACTERISTICS:
        (A) LENGTH: 238 amino acids
        (B) TYPE: amino acid
        (D) TOPOLOGY: linear (ii) MOLECULE TYPE: protein (xi) SEQUENCE DESCRIPTION: SEQ ID NO:10:

```
Met Gly Pro Val Ser Thr Ser Arg Arg Gly Leu Arg Leu Gly Ile Ser
-22         -20                 -15                 -10

Leu Ile Leu Leu Gln Val Gly Val Val Gly Ala Cys Thr Val Ser Val
        -5                   1                   5                  10

Leu Gln Pro Gly Tyr Leu Glu Val Asp Tyr Thr Ser Gln Thr Val Thr
                15                  20                  25

Met Glu Cys Thr Phe Ser Thr Thr Gly Cys Pro Ala Val Gln Pro Lys
            30                  35                  40

Ser Leu Trp Phe Arg Cys Gly Thr His Gln Pro Glu Ala Leu Cys Leu
        45                  50                  55

Asp Gly Cys Arg Asn Glu Ala Asp Lys Phe Thr Val Lys Glu Thr Leu
    60                  65                  70

Asp Gln Asn Arg Val Ser Leu Thr Val Asn Arg Leu Ser Pro Asn Asp
75                  80                  85                  90

Ser Ala Ile Tyr Ile Cys Gly Ile Ala Phe Pro Asn Glu Pro Val Pro
                95                  100                 105

Thr Ala Lys Gln Thr Gly Asp Gly Thr Thr Leu Val Val Arg Glu Arg
            110                 115                 120

Leu Phe Ser Arg Glu Val His Ser Leu Leu Ile Val Leu Leu Ala Leu
        125                 130                 135

Leu Ala Val Tyr Val Thr Gly Val Cys Val Ile Phe Ile Val Leu Phe
    140                 145                 150

Arg Ser Lys Ser Asn Thr Pro Arg Ser Arg Glu Thr Lys Glu Asp Ser
155                 160                 165                 170

Lys Lys Lys Ser Ala Arg Arg Ile Phe Gln Glu Ile Ala Gln Glu Leu
                175                 180                 185
```

```
Tyr His Lys Arg Tyr Val Glu Thr Ser His Gln Pro Glu Gln Asp Gly
            190                 195                 200

Asn Tyr Glu Asn Arg Lys Ala Leu Pro Ser Pro Gly Arg Pro
        205                 210                 215

(2) INFORMATION FOR SEQ ID NO:11:

(i) SEQUENCE CHARACTERISTICS:
        (A) LENGTH: 3172 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 43..1290

(ix) FEATURE:
        (A) NAME/KEY: mat_peptide
        (B) LOCATION: 112..1290

(ix) FEATURE:
        (A) NAME/KEY: misc_feature
        (B) LOCATION: 481
        (D) OTHER INFORMATION: /note= "may be T"

(ix) FEATURE:
        (A) NAME/KEY: misc_feature
        (B) LOCATION: 994
        (D) OTHER INFORMATION: /note= "may be A"

(ix) FEATURE:
        (A) NAME/KEY: misc_feature
        (B) LOCATION: 49..51
        (D) OTHER INFORMATION: /note= "codon might be CGG"

(xi) SEQUENCE DESCRIPTION: SEQ ID NO:11:

CGCCCGGGCA GGTAGCGGCC GCTGAATTCT AGAACGCCCA CC ATG CCC CGG CAG        54
                                              Met Pro Arg Gln
                                              -23         -20

CTC AGC GCG GCG GCC GCG CTC TTC GCG TCC CTG GCC GTA ATT TTG CAC      102
Leu Ser Ala Ala Ala Ala Leu Phe Ala Ser Leu Ala Val Ile Leu His
            -15                 -10                 -5

GAT GGC AGT CAA ATG AGA GCA AAA GCA TTT CCA GAA ACC AGA GAT TAT      150
Asp Gly Ser Gln Met Arg Ala Lys Ala Phe Pro Glu Thr Arg Asp Tyr
            1               5                   10

TCT CAA CCT ACT GCA GCA GCA ACA GTA CAG GAC ATA AAA AAA CCT GTC      198
Ser Gln Pro Thr Ala Ala Ala Thr Val Gln Asp Ile Lys Lys Pro Val
        15                  20                  25

CAG CAA CCA GCT AAG CAA GCA CCT CAC CAA ACT TTA GCA GCA AGA TTC      246
Gln Gln Pro Ala Lys Gln Ala Pro His Gln Thr Leu Ala Ala Arg Phe
    30                  35                  40                  45

ATG GAT GGT CAT ATC ACC TTT CAA ACA GCG GCC ACA GTA AAA ATT CCA      294
Met Asp Gly His Ile Thr Phe Gln Thr Ala Ala Thr Val Lys Ile Pro
                50                  55                  60

ACA ACT ACC CCA GCA ACT ACA AAA AAC ACT GCA ACC ACC AGC CCA ATT      342
Thr Thr Thr Pro Ala Thr Thr Lys Asn Thr Ala Thr Thr Ser Pro Ile
                65                  70                  75

ACC TAC ACC CTG GTC ACA ACC CAG GCC ACA CCC AAC AAC TCA CAC ACA      390
Thr Tyr Thr Leu Val Thr Thr Gln Ala Thr Pro Asn Asn Ser His Thr
                80                  85                  90

GCT CCT CCA GTT ACT GAA GTT ACA GTC GGC CCT AGC TTA GCC CCT TAT      438
Ala Pro Pro Val Thr Glu Val Thr Val Gly Pro Ser Leu Ala Pro Tyr
                95                  100                 105
```

```
TCA CTG CCA CCC ACC ATC ACC CCA CCA GCT CAT ACA ACT GGA ACC AGT       486
Ser Leu Pro Pro Thr Ile Thr Pro Pro Ala His Thr Thr Gly Thr Ser
110             115                 120                 125

TCA TCA ACC GTC AGC CAC ACA ACT GGG AAC ACC ACT CAA CCC AGT AAC       534
Ser Ser Thr Val Ser His Thr Thr Gly Asn Thr Thr Gln Pro Ser Asn
                130                 135                 140

CAG ACC ACC CTT CCA GCA ACT TTA TCG ATA GCA CTG CAC AAA AGC ACA       582
Gln Thr Thr Leu Pro Ala Thr Leu Ser Ile Ala Leu His Lys Ser Thr
            145                 150                 155

ACC GGT CAG AAG CCT GTT CAA CCC ACC CAT GCC CCA GGA ACA ACG GCA       630
Thr Gly Gln Lys Pro Val Gln Pro Thr His Ala Pro Gly Thr Thr Ala
        160                 165                 170

GCT GCC CAC AAT ACC ACC CGC ACA GCT GCA CCT GCC TCC ACG GTT CCT       678
Ala Ala His Asn Thr Thr Arg Thr Ala Ala Pro Ala Ser Thr Val Pro
    175                 180                 185

GGG CCC ACC CTT GCA CCT CAG CCA TCG TCA GTC AAG ACT GGA ATT TAT       726
Gly Pro Thr Leu Ala Pro Gln Pro Ser Ser Val Lys Thr Gly Ile Tyr
190                 195                 200                 205

CAG GTT CTA AAC GGA AGC AGA CTC TGT ATA AAA GCA GAG ATG GGG ATA       774
Gln Val Leu Asn Gly Ser Arg Leu Cys Ile Lys Ala Glu Met Gly Ile
                210                 215                 220

CAG CTG ATT GTT CAA GAC AAG GAG TCG GTT TTT TCA CCT CGG AGA TAC       822
Gln Leu Ile Val Gln Asp Lys Glu Ser Val Phe Ser Pro Arg Arg Tyr
            225                 230                 235

TTC AAC ATC GAC CCC AAC GCA ACG CAA GCC TCT GGG AAC TGT GGC ACC       870
Phe Asn Ile Asp Pro Asn Ala Thr Gln Ala Ser Gly Asn Cys Gly Thr
        240                 245                 250

CGA AAA TCC AAC CTT CTG TTG AAT TTT CAG GGC GGA TTT GTG AAT CTC       918
Arg Lys Ser Asn Leu Leu Leu Asn Phe Gln Gly Gly Phe Val Asn Leu
    255                 260                 265

ACA TTT ACC AAG GAT GAA GAA TCA TAT TAT ATC AGT GAA GTG GGA GCC       966
Thr Phe Thr Lys Asp Glu Glu Ser Tyr Tyr Ile Ser Glu Val Gly Ala
270                 275                 280                 285

TAT TTG ACC GTC TCA GAT CCA GAG ACA ATT TAC CAA GGA ATC AAA CAT      1014
Tyr Leu Thr Val Ser Asp Pro Glu Thr Ile Tyr Gln Gly Ile Lys His
                290                 295                 300

GCG GTG GTG ATG TTC CAG ACA GCA GTC GGG CAT TCC TTC AAG TGC GTG      1062
Ala Val Val Met Phe Gln Thr Ala Val Gly His Ser Phe Lys Cys Val
            305                 310                 315

AGT GAA CAG AGC CTC CAG TTG TCA GCC CAC CTG CAG GTG AAA ACA ACC      1110
Ser Glu Gln Ser Leu Gln Leu Ser Ala His Leu Gln Val Lys Thr Thr
        320                 325                 330

GAT GTC CAA CTT CAA GCC TTT GAT TTT GAA GAT GAC CAC TTT GGA AAT      1158
Asp Val Gln Leu Gln Ala Phe Asp Phe Glu Asp Asp His Phe Gly Asn
    335                 340                 345

GTG GAT GAG TGC TCG TCT GAC TAC ACA ATT GTG CTT CCT GTG ATT GGG      1206
Val Asp Glu Cys Ser Ser Asp Tyr Thr Ile Val Leu Pro Val Ile Gly
350                 355                 360                 365

GCC ATC GTG GTT GGT CTC TGC CTT ATG GGT ATG GGT GTC TAT AAA ATC      1254
Ala Ile Val Val Gly Leu Cys Leu Met Gly Met Gly Val Tyr Lys Ile
                370                 375                 380

CGC CTA AGG TGT CAA TCA TCT GGA TAC CAG AGA ATC TAATTGTTGC           1300
Arg Leu Arg Cys Gln Ser Ser Gly Tyr Gln Arg Ile
            385                 390

CCGGGGGGAA TGAAAATAAT GGAATTTAGA GAACTCTTTC ATCCTTCCAG GATGGATGTT    1360

GGAAATTCCC TCAGAGTGTG GGTCCTTCAA ACAATGTAAA CCACCATCTT CTATTCAAAT    1420

GAAGTGAGTC ATGTGTGATT TAAGTTCAGG CAGCACATCA ATTTCTAAAT ACTTTTTGTT    1480

TATTTTATGA AAGATATAGT GAGCTGTTTA TTTTCTAGTT TCCTTTAGAA TATTTTAGCC    1540
```

-continued

```
ACTCAAAGTC AACATTTGAG ATATGTTGAA TTAACATAAT ATATGTAAAG TAGAATAAGC     1600

CTTCAAATTA TAAACCAAGG GTCAATTGTA ACTAATACTA CTGTGTGTGC ATTGAAGATT     1660

TTATTTTACC CTTGATCTTA ACAAAGCCTT TGCTTTGTTA TCAAATGGAC TTTCAGTGCT     1720

TTTACTATCT GTGTTTTATG GTTTCATGTA ACATACATAT TCCTGGTGTA GCACTTAACT     1780

CCTTTTCCAC TTTAAATTTG TTTTTGTTTT TTGAGACGGA GTTTCACTCT TGTCACCCAG     1840

GCTGGAGTAC AGTGGCACGA TCTCGGCTTA TGGCAACCTC CGCCTCCCGG GTTCAAGTGA     1900

TTCTCCTGCT TCAGCTTCCC GAGTAGCTGG GATTACAGGC ACACACTACC ACGCCTGGCT     1960

AATTTTTGTA TTTTTATTAT AGACGGGGTT TCACCATGTT GGCCAGACTG GTCTTGAACT     2020

CTTGACCTCA GGTGATCCAC CCACCTCAGC CTCCCAAAGT GCTGGGATTA CAGGCATGAG     2080

CCATTGCGCC CGGCCTTAAA TGTTTTTTTT AATCATCAAA AGAACAACA TATCTCAGGT      2140

TGTCTAAGTG TTTTTATGTA AAACCAACAA AAAGAACAAA TCAGCTTATA TTTTTTATCT     2200

TGATGACTCC TGCTCCAGAA TCGCTAGACT AAGAATTAGG TGGCTACAGA TGGTAGAACT     2260

AAACAATAAG CAAGAGACAA TAATAATGGC CCTTAATTAT TAACAAAGTG CCAGAGTCTA     2320

GGCTAAGCAC TTTATCTATA TCTCATTTCA TTCTCACAAC TTATAGGTGA ATGAGTAAAC     2380

TGAGACTTAA GGGAACTGAA TCACTTAAAT GTCACCTGGC TAACTGATGG CAGAGCCAGA     2440

GCTTGAATTC ATGTTGGTCT GACATCAAGG TCTTTGGTCT TCTCCCTACA CCAAGTTACC     2500

TACAAGAACA ATGACACCAC ACTCTGCCTG AAGGCTCACA CCTCATACCA GCATACGCTC     2560

ACCTTACAGG GAAATGGGTT TATCCAGGAT CATGAGACAT TAGGGTAGAT GAAAGGAGAG     2620

CTTTGCAGAT AACAAAATAG CCTATCCTTA ATAAATCCTC CACTCTCTGG AAGGAGACTG     2680

AGGGGCTTTG TAAAACATTA GTCAGTTGCT CATTTTTATG GGATTGCTTA GCTGGGCTGT     2740

AAAGATGAAG GCATCAAATA AACTCAAAGT ATTTTTAAAT TTTTTTGATA ATAGAGAAAC     2800

TTCGCTAACC AACTGTTCTT TCTTGAGTGA TAGCCCCATC TTGTGGTAAC TTGCTGCTTC     2860

TGCACTTCAT ATCCATATTT CCTATTGTTC ACTTTATTCT GTAGAGCAGC CTGCCAAGAA     2920

TTTTATTTCT GCTGTTTTTT TTGCTGCTAA AGAAAGGAAC TAAGTCAGGA TGTTAACAGA     2980

AAAGTCCACA TAACCCTAGA ATTCTTAGTC AAGGAATAAT TCAAGTCAGC CTAGAGACCA     3040

TGTTGACTTT CCTCATGTGT TTCCTTATGA CTCAGTAAGT TGGCAAGGTC CTGACTTTAG     3100

TCTTAATAAA ACATTGAATT GTAGTAAAGG TTTTTGTAAT AAAAACTTAC TTTGGAAAAA     3160

AAAAAAAAA AA                                                          3172
```

(2) INFORMATION FOR SEQ ID NO:12:

(i) SEQUENCE CHARACTERISTICS:
        (A) LENGTH: 416 amino acids
        (B) TYPE: amino acid
        (D) TOPOLOGY: linear (ii) MOLECULE TYPE: protein (xi) SEQUENCE DESCRIPTION: SEQ ID NO:12:

```
Met Pro Arg Gln Leu Ser Ala Ala Ala Leu Phe Ala Ser Leu Ala
-23         -20                 -15                 -10

Val Ile Leu His Asp Gly Ser Gln Met Arg Ala Lys Ala Phe Pro Glu
        -5                   1                   5

Thr Arg Asp Tyr Ser Gln Pro Thr Ala Ala Thr Val Gln Asp Ile
 10                  15                  20                  25

Lys Lys Pro Val Gln Gln Pro Ala Lys Gln Ala Pro His Gln Thr Leu
             30                  35                  40
```

-continued

```
Ala Ala Arg Phe Met Asp Gly His Ile Thr Phe Gln Thr Ala Ala Thr
             45                  50                  55

Val Lys Ile Pro Thr Thr Thr Pro Ala Thr Thr Lys Asn Thr Ala Thr
             60                  65                  70

Thr Ser Pro Ile Thr Tyr Thr Leu Val Thr Thr Gln Ala Thr Pro Asn
     75                  80                  85

Asn Ser His Thr Ala Pro Pro Val Thr Glu Val Thr Val Gly Pro Ser
 90                  95                 100                 105

Leu Ala Pro Tyr Ser Leu Pro Pro Thr Ile Thr Pro Pro Ala His Thr
                110                 115                 120

Thr Gly Thr Ser Ser Ser Thr Val Ser His Thr Thr Gly Asn Thr Thr
                125                 130                 135

Gln Pro Ser Asn Gln Thr Thr Leu Pro Ala Thr Leu Ser Ile Ala Leu
            140                 145                 150

His Lys Ser Thr Thr Gly Gln Lys Pro Val Gln Pro Thr His Ala Pro
            155                 160                 165

Gly Thr Thr Ala Ala Ala His Asn Thr Thr Arg Thr Ala Ala Pro Ala
170                 175                 180                 185

Ser Thr Val Pro Gly Pro Thr Leu Ala Pro Gln Pro Ser Ser Val Lys
                190                 195                 200

Thr Gly Ile Tyr Gln Val Leu Asn Gly Ser Arg Leu Cys Ile Lys Ala
                205                 210                 215

Glu Met Gly Ile Gln Leu Ile Val Gln Asp Lys Glu Ser Val Phe Ser
            220                 225                 230

Pro Arg Arg Tyr Phe Asn Ile Asp Pro Asn Ala Thr Gln Ala Ser Gly
        235                 240                 245

Asn Cys Gly Thr Arg Lys Ser Asn Leu Leu Leu Asn Phe Gln Gly Gly
250                 255                 260                 265

Phe Val Asn Leu Thr Phe Thr Lys Asp Glu Glu Ser Tyr Tyr Ile Ser
                270                 275                 280

Glu Val Gly Ala Tyr Leu Thr Val Ser Asp Pro Glu Thr Ile Tyr Gln
            285                 290                 295

Gly Ile Lys His Ala Val Val Met Phe Gln Thr Ala Val Gly His Ser
        300                 305                 310

Phe Lys Cys Val Ser Glu Gln Ser Leu Gln Leu Ser Ala His Leu Gln
    315                 320                 325

Val Lys Thr Thr Asp Val Gln Leu Gln Ala Phe Asp Phe Glu Asp Asp
330                 335                 340                 345

His Phe Gly Asn Val Asp Glu Cys Ser Ser Asp Tyr Thr Ile Val Leu
                350                 355                 360

Pro Val Ile Gly Ala Ile Val Val Gly Leu Cys Leu Met Gly Met Gly
            365                 370                 375

Val Tyr Lys Ile Arg Leu Arg Cys Gln Ser Ser Gly Tyr Gln Arg Ile
        380                 385                 390
```

ISOLATED MAMMALIAN DENDRITIC CELL GENES; RELATED REAGENTS

This filing is a conversion of U.S. Provisional Patent Applications DX0669P, U.S. Ser. No. 60/031,806, filed Nov. 27, 1996, and DX0669P1, U.S. Ser. No. 60/032,767, filed Dec. 11, 1996, each of which is incorporated herein by reference, to a regular utility patent application.

FIELD OF THE INVENTION

The present invention contemplates compositions related to genes found in dendritic cells, cells which function in the immune system. These genes function in controlling development, differentiation, and/or physiology of mammalian immune system. In particular, the application provides nucleic acids, proteins, antibodies, and methods of using them.

BACKGROUND OF THE INVENTION

The circulating component of the mammalian circulatory system comprises various cell types, including red and white blood cells of the erythroid and myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed.) (1993) *Fundamental Immunology* (3d ed.) Raven Press, N.Y.

Dendritic cells are antigen-presenting cells, and are found in all tissues of the body. They can be classified into various categories, including: interstitial dendritic cells of the heart, kidney, gut, and lung; Langerhans cells in the skin and mucous membranes; interdigitating dendritic cells in the thymic medulla and secondary lymphoid tissue; and blood and lymph dendritic cells. Although dendritic cells in each of these compartments are CD45+ leukocytes that apparently arise from bone marrow, they may exhibit differences that relate to maturation state and microenvironment.

Dendritic cells (DC), which are specialized antigen-presenting cells, efficiently process and present antigens to, e.g., T cells. They stimulate responses from naive and memory T cells in the paracortical area of secondary lymphoid organs. There is some evidence for a role in induction of tolerance.

The primary and secondary B-cell follicles contain follicular dendritic cells that trap and retain intact antigen as immune complexes for long periods of time. These dendritic cells present native antigen to B cells and are likely to be involved being the affinity maturation of antibodies, the generation of immune memory, and the maintenance of humoral immune responses.

However, dendritic cells are poorly characterized, both in terms of proteins they express, and many of their functions and mechanisms of action. The absence of knowledge about the structural, biological, and physiological properties of these cells limits their understanding. Thus, medical conditions where regulation, development, or physiology of dendritic cells is unusual remain unmanageable.

SUMMARY OF THE INVENTION

The present invention is based, in part, upon the discovery of three clones isolated from activated dendritic cells, which identify mammalian genes of structural and functional relationship. It embraces agonists and antagonists of these molecules designated A05F12 (diubiquitin), A07C03 (Ig family gene), and E02B02 (LAMP-like gene), e.g., mutations (muteins) of the natural sequences, fusion proteins, chemical mimetics, antibodies, and other structural or functional analogs. It is also directed to isolated genes encoding proteins of the invention. Various uses of these different protein or nucleic acid composition are also provided.

The present invention provides a composition of matter selected from: a substantially pure or recombinant A05F12 protein or peptide exhibiting at least about 85% sequence identity over a length of at least about 12 amino acids to SEQ ID NO: 2 or 4; a natural sequence A05F12 comprising SEQ ID NO: 2 or 4; a fusion protein comprising A05F12 sequence; a substantially pure or recombinant A07C03 protein or peptide exhibiting at least about 85% sequence identity over a length of at least about 12 amino acids to SEQ ID NO: 6, 8, or 10; a natural sequence A07C03 comprising SEQ ID NO: 6, 8, or 10; a fusion protein comprising A07C03 sequence; a substantially pure or recombinant E02B02 protein or peptide exhibiting at least about 85% sequence identity over a length of at least about 12 amino acids to SEQ ID NO: 12; a natural sequence E02B02 comprising SEQ ID NO: 12; or a fusion protein comprising E02B02 sequence. In certain preferred embodiments, the substantially pure or isolated protein will comprise a segment exhibiting sequence identity to a corresponding portion of an: A05F12, wherein: the homology is at least about 90% identity and the portion is at least about 9 amino acids; the homology is at least about 80% identity and the portion is at least about 17 amino acids; or the homology is at least about 70% identity and the portion is at least about 25 amino acids; A07C03, wherein: the homology is at least about 90% identity and the portion is at least about 9 amino acids; the homology is at least about 80% identity and the portion is at least about 17 amino acids; or the homology is at least about 70% identity and the portion is at least about 25 amino acids; or E02B02, wherein: the homology is at least about 90% identity and the portion is at least about 9 amino acids; the homology is at least about 80% identity and the portion is at least about 17 amino acids; or the homology is at least about 70% identity and the portion is at least about 25 amino acids. Other preferred embodiments include where: A05F12 comprises a mature sequence of Table 1; the A05F12 protein or peptide: is from a warm blooded animal selected from a primate or rodent, such as a human or mouse; comprises at least one polypeptide segment of SEQ ID NO: 2 or 4; exhibits a plurality of portions exhibiting said identity; is a natural allelic variant of a primate or rodent A05F12; has a length at least about 30 amino acids; exhibits at least two non-overlapping epitopes which are specific for a primate or rodent A05F12; exhibits a sequence identity at least about 90% over a length of at least about 20 amino acids to a primate or rodent A05F12; has a molecular weight of at least 100 kD with natural glycosylation; is a synthetic polypeptide; is attached to a solid substrate; is conjugated to another chemical moiety; is a 5-fold or less substitution from natural sequence; or is a deletion or insertion variant from a natural sequence; A07C03 comprises a mature sequence of Table 2; the A07C03 protein or peptide: is from a warm blooded animal selected from a primate or rodent, such as a human or mouse; comprises at least one polypeptide segment of SEQ ID NO: 8 or 10; exhibits a plurality of portions exhibiting said identity; is a natural allelic variant of a primate or rodent A07C03; has a length at least about 30 amino acids; exhibits at least two non-overlapping epitopes which are specific for a primate or rodent A07C03; exhibits a sequence identity at least about 90% over a length of at least about 20 amino acids to a primate or rodent A07C03; has a molecular weight of at least 100 kD with natural glycosylation; is a synthetic polypeptide; is attached to a solid substrate; is conjugated to another chemical moiety; is a 5-fold or less substitution from natural sequence; or is a deletion or insertion variant from a natural sequence; E02B02 comprises a mature sequence of Table 3; or the E02B02 protein or peptide: is from a warm blooded animal selected from a primate, such as a human; comprises at least one polypeptide segment of SEQ ID NO: 12; exhibits a plurality of portions exhibiting said identity; is a natural allelic variant of a primate E02B02; has a length at least about 30 amino acids; exhibits at least two non-overlapping epitopes which are specific for a primate E02B02; exhibits a sequence identity at least about 90% over a length of at least about 20 amino acids to a primate E02B02; has a molecular weight of at least 100 kD with natural glycosylation; is a synthetic polypeptide; is attached to a solid substrate; is conjugated to another chemical moiety; is a 5-fold or less substitution from natural sequence; or is a deletion or insertion variant from a natural sequence. Other preferred embodiments include a composition comprising: a sterile A05F12 protein or peptide; the A05F12 protein or peptide and a carrier, wherein the carrier is: an aqueous compound, including water, saline, and/or buffer; and/or formulated for oral, rectal, nasal, topical, or parenteral administration; a sterile A07C03 protein or peptide; the A07C03 protein or peptide and a carrier, wherein the carrier is: an aqueous compound, including water, saline, and/or buffer; and/or formulated for oral, rectal, nasal, topical, or parenteral administration; a sterile E02B02 protein or peptide; or the E02B02 protein or peptide and a carrier, wherein the carrier is: an aqueous compound, including water, saline, and/or buffer; and/or formulated for oral, rectal, nasal, topical, or parenteral administration.

In fusion protein embodiments, the invention provides such comprising: mature protein sequence of Table 1, 2, or 3; a detection or purification tag, including a FLAG, His6, or Ig sequence; or sequence of another receptor protein. Kit embodiments include those comprising a protein or polypeptide as described, and: a compartment comprising the protein or polypeptide; and/or instructions for use or disposal of reagents in the kit.

Other aspects of the invention include a binding compound comprising an antigen binding site from an antibody, which specifically binds to a natural: A05F12 protein, wherein: the protein is a primate or rodent protein; the binding compound is an Fv, Fab, or Fab2 fragment; the binding compound is conjugated to another chemical moiety; or the antibody: is raised against a peptide sequence of a mature polypeptide of Table 1; is raised against a mature primate or rodent A05F12; is raised to a purified human A05F12; is raised to a purified mouse A05F12; is immunoselected; is a polyclonal antibody; binds to a denatured A05F12; exhibits a Kd to antigen of at least 30 $\mu$M; is attached to a solid substrate, including a bead or plastic membrane; is in a sterile composition; or is detectably labeled, including a radioactive or fluorescent label; A07C03 protein, wherein: the protein is a primate or rodent protein; the binding compound is an Fv, Fab, or Fab2 fragment; the binding compound is conjugated to another chemical moiety; or the antibody: is raised against a peptide sequence of a mature polypeptide of Table 2; is raised against a mature primate or rodent A07C03; is raised to a purified human A07C03; is raised to a purified mouse A07C03; is immunoselected; is a polyclonal antibody; binds to a denatured A07C03; exhibits a Kd to antigen of at least 30 $\mu$M; is attached to a solid substrate, including a bead or plastic membrane; is in a sterile composition; or is detectably labeled, including a radioactive or fluorescent label; or E02B02 protein, wherein: the protein is a primate protein; the binding compound is an Fv, Fab, or Fab2 fragment; the binding compound is conjugated to another chemical moiety; or the antibody: is raised against a peptide sequence of a mature polypeptide of Table 3; is raised against a mature primate E02B02; is raised to a purified human E02B02; is immunoselected; is a polyclonal antibody; binds to a denatured E02B02; exhibits a Kd to antigen of at least 30 $\mu$M; is attached to a solid substrate, including a bead or plastic membrane; is in a sterile composition; or is detectably labeled, including a radioactive or fluorescent label.

Certain kit embodiments of the invention include those comprising such a binding compound, and: a compartment comprising the binding compound; and/or instructions for use or disposal of reagents in the kit. Preferably, the kit is capable of making a qualitative or quantitative analysis. Other compositions are provided, e.g., those comprising: the binding compound, as described, and a carrier, wherein the carrier is: an aqueous compound, including water, saline, and/or buffer; and/or formulated for oral, rectal, nasal, topical, or parenteral administration.

Nucleic acid embodiments include an isolated or recombinant nucleic acid encoding a protein or peptide or fusion protein described, wherein: the A05F12 protein or peptide is from a mammal, including a primate or rodent; the nucleic acid: encodes an antigenic peptide sequence of Table 1; encodes a plurality of antigenic peptide sequences of Table 1; exhibits at least about 80% identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a mammal, including a primate or rodent; comprises a natural full length coding sequence; is a hybridization probe for a gene encoding the A05F12; or is a PCR primer, PCR product, or mutagenesis primer; the A05C03 is from a mammal, including a primate or rodent; the nucleic acid: encodes an antigenic peptide sequence of Table 2; encodes a plurality of antigenic peptide sequences of Table 2; exhibits at least about 80% identity to a natural cDNA encoding the segment; is an expression vector; further comprises an origin of replication; is from a natural source; comprises a detectable label; comprises synthetic nucleotide sequence; is less than 6 kb, preferably less than 3 kb; is from a mammal, including a primate or rodent; comprises a natural full length coding sequence; is a hybridization probe for a gene encoding the A07C03; or is a PCR primer, PCR product, or mutagenesis primer; the E02B02 is from a mammal, including a primate; or the nucleic acid: encodes an antigenic peptide sequence of Table 3; encodes a plurality of antigenic peptide sequences of Table 3; exhibits at least about 80% identity to a natural cDNA encoding the segment; is an expression vector; further comprises an origin of replication; is from a natural source; comprises a detectable label; comprises synthetic nucleotide sequence; is less than 6 kb, preferably less than 3 kb is from a mammal, including a primate; comprises a natural full length coding sequence; is a hybridization probe for a gene encoding the E02B02; or is a PCR primer, PCR product, or mutagenesis primer. The invention further provides a cell, tissue, or organ comprising such a recombinant nucleic acid, including where the cell is: a prokaryotic cell; a eukaryotic cell; a bacterial cell; a yeast cell; an insect cell; a mammalian cell; a mouse cell; a primate cell; or a human cell.

Various kits include those comprising a described nucleic acid, and: a compartment comprising the nucleic acid; a compartment further comprising a primate or rodent A05F12 protein or polypeptide; a compartment further comprising a primate or rodent A07C03 protein or polypeptide; a compartment further comprising a primate E02B02 protein or polypeptide; and/or instructions for use or disposal of reagents in the kit. Preferably, the kit is capable of making a qualitative or quantitative analysis.

Certain preferred nucleic acids include those which: hybridize under wash conditions of 30° C. and less than 2M salt to SEQ ID NO: 1 or 3; hybridize under wash conditions of 30° C. and less than 2M salt to SEQ ID NO: 5, 7, or 9; hybridize under wash conditions of 30° C. and less than 2M salt to SEQ ID NO: 11; exhibit at least about 85% identity over a stretch of at least about 30 nucleotides to a primate or rodent A05F12; exhibit at least about 85% identity over a stretch of at least about 30 nucleotides to a primate or rodent A07C03; or exhibit at least about 85% identity over a stretch of at least about 30 nucleotides to a primate E02B02. Other preferred nucleic acids are those wherein: the wash conditions are at 45° C. and/or 500 mM salt; the wash conditions are at 55° C. and/or 150 mM salt; the identity is at least 90% and/or the stretch is at least 55 nucleotides; or the identity is at least 95% and/or the stretch is at least 75 nucleotides.

Various methods are provided, e.g., of modulating physiology or development of a cell or tissue culture cells comprising contacting the cell with: a binding composition which binds to a primate or rodent A05F12; a binding composition, which binds to a primate or rodent A07C03; a binding composition, which binds to a primate E01B02; an antisense nucleic acid which blocks expression of a primate or rodent A05F12; an antisense nucleic acid which blocks expression of a primate or rodent A07C03; or an antisense nucleic acid which blocks expression of a primate E02B02.

DETAILED DESCRIPTION

OUTLINE
I. General
II. Definitions
III. Nucleic Acids
IV. Making Proteins
V. Antibodies
VI. Purified Proteins
VII. Physical Variants
VIII. Binding Agent:DC Protein Complexes
IX. Uses
X. Kits
XI. Binding Partner Isolation I. General The present invention provides DNA sequences encoding mammalian proteins expressed on dendritic cells (DC). For a review of dendritic cells, see Steinman (1991) *Annual Review of Immunology* 9:271–296; and Banchereau and Schmitt (eds. 1994) *Dendritic Cells in Fundamental and Clinical Immunology* Plenum Press, N.Y. These proteins are designated dendritic cell proteins because they were initially found on these cells and appear to exhibit some specificity in their expression.

Specific human or mouse embodiments of these proteins are provided below. The descriptions below are directed, for exemplary purposes, to human DC genes, but are likewise applicable to structurally, e.g., sequence, related embodiments from other sources or mammalian species, including polymorphic or individual variants. These will include, e.g., proteins which exhibit a relatively few changes in sequence, e.g., less than about 5%, and number, e.g., less than 20 residue substitutions, typically less than 15, preferably less than 10, and more preferably less than 5 substitutions. These will also include versions which are truncated from full length, as described, and fusion proteins containing substantial segments of these sequences.

II. Definitions

The term "binding composition" refers to molecules that bind with specificity to a these DC proteins, e.g., in an antibody-antigen interaction, or compounds, e.g., proteins, which specifically associate with the respective protein. Typically, the association will be in a natural physiologically relevant protein-protein interaction, either covalent or non-covalent, and may include members of a multiprotein complex, including carrier compounds or dimerization partners. The molecule may be a polymer, or chemical reagent. A functional analog may be a protein with structural modifications, or may be a wholly unrelated molecule, e.g., which has a molecular shape which interacts with the appropriate interacting determinants. The variants may serve as agonists or antagonists of the protein, see, e.g., Goodman, et al. (eds.) (1990) *Goodman & Gilmanl's: The Pharmacological Bases of Therapeutics* (8th ed.) Pergamon Press, Tarrytown, N.Y.

The term "binding agent:DC protein complex", as used herein, refers to a complex of a binding agent and the DC protein. Specific binding of the binding agent means that the binding agent has a specific binding site that recognizes a site on the respective DC protein. For example, antibodies raised to the DC protein and recognizing an epitope on the DC protein are capable of forming a binding agent:DC protein complex by specific binding. Typically, the formation of a binding agent:DC protein complex allows the measurement of DC protein in a mixture of other proteins and biologics. The term "antibody:DC protein complex" refers to a binding agent:DC protein complex in which the binding agent is an antibody. The antibody may be monoclonal, polyclonal or even an antigen binding fragment of an antibody.

"Homologous" nucleic acid sequences, when compared, exhibit significant similarity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. An isolated nucleic acid will generally be a homogeneous composition of molecules, but will, in some embodiments, contain minor heterogeneity. This heterogeneity is typically found at the polymer ends or portions not critical to a desired biological function or activity.

As used herein, the term "DC protein" shall encompass, when used in a protein context, a protein having amino acid sequences as shown in SEQ ID NO: 2, 4, 6, 8, 10, or 12, or a significant fragment of such a protein. It refers to a polypeptide which interacts with the respective DC protein specific binding components. These binding components, e.g., antibodies, typically bind to the DC protein with high affinity, e.g., at least about 100 nM, usually better than about 30 nM, preferably better than about 10 nM, and more preferably at better than about 3 nM.

The term "polypeptide" or "protein" as used herein includes a significant fragment or segment of said DC protein, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W.H. Freeman & Co., San Francisco, Calif.; and Cantor and Schimmel (1980) *Biophysical Chemistry* parts 1–3, W.H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the protein.

"Substantially pure" typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1, 3, 5, 7, 9, or 11. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) *J. Mol. Biol.* 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

Counterpart DC proteins from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human DC protein immunogen with the amino acid sequence depicted in SEQ ID NO: 2 can be selected to obtain antibodies specifically immunoreactive with that DC protein and not with other proteins. These antibodies recognize proteins highly similar to the homologous human DC protein.

III. Nucleic Acids

These DC genes are specifically expressed on dendritic cells. The preferred embodiments, as disclosed, will be useful in standard procedures to isolate genes from other species, e.g., warm blooded animals, such as birds and mammals. Cross hybridization will allow isolation of related proteins from individuals, strains, or species. A number of different approaches are available successfully to isolate a suitable nucleic acid clone based upon the information provided herein. Southern blot hybridization studies should identify homologous genes in other species under appropriate hybridization conditions.

Purified protein or defined peptides are useful for generating antibodies by standard methods, as described below. Synthetic peptides or purified protein can be presented to an immune system to generate polyclonal and monoclonal antibodies. See, e.g., Coligan (1991) *Current Protocols in Immunology* Wiley/Greene, NY; and Harlow and Lane (1989) *Antibodies: A Laboratory Manual* Cold Spring Harbor Press, NY, which are incorporated herein by reference. Alternatively, a CD protein binding composition can be useful as a specific binding reagent, and advantage can be taken of its specificity of binding, for, e.g., purification of a DC protein.

The specific binding composition can be used for screening an expression library made from a cell line which expresses the respective DC protein. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

TABLE 1

Sequence encoding a humnan di-ubiquitin protein, containing two ubiquitin domains which extend from about 1 (met) to about 83 (pro) and from about 89 (pro) to about 165 (gly). The putative polypeptide sequence comprises four cysteine residues which are not characteristic of a human ubiquitin domain, e.g., that of UCRP of Narasimhan, et al. (1996) J. Biol. Chem. 271:324–330. Note the ubiquitin conserved residues 48 (lys) and 70 (lys) are present here, which residues have been implicated in protein binding. The terminal glycine doublet is also characteristic. See SEQ ID NO: 1 and 2. This sequence was derived from an activated CD1a dendritic cell library.

```
GGCCCCTTGT CTGCAGAG ATG GCT CCC AAT GCT TCC TGC CTC TGT GTG CAT     51
                    Met Ala Pro Asn Ala Ser Cys Leu Cys Val His
                     1                5                    10

GTC CGT TCC GAG GAA TGG GAT TTA ATG ACC TTT GAT GCC AAC CCA TAT     99
Val Arg Ser Glu Glu Trp Asp Leu Met Thr Phe Asp Ala Asn Pro Tyr
             15                  20                  25

GAC AGC GTG AAA AAA ATC AAA GAA CAT GTC CGG TCT AAG ACC AAG GTT    147
Asp Ser Val Lys Lys Ile Lys Glu His Val Arg Ser Lys Thr Lys Val
             30                  35                  40

CCT GTG CAG GAC CAG GTT CTT TTG CTG GGC TCC AAG ATC TTA AAG CCA    195
Pro Val Gln Asp Gln Val Leu Leu Leu Gly Ser Lys Ile Leu Lys Pro
         45                  50                  55

CGG AGA AGC CTC TCA TCT TAT GGC ATT GAC AAA GAG AAG ACC ATC CAC    243
Arg Arg Ser Leu Ser Ser Tyr Gly Ile Asp Lys Glu Lys Thr Ile His
 60                  65                  70                  75
```

TABLE 1-continued

Sequence encoding a humnan di-ubiquitin protein, containing two ubiquitin domains which extend from about 1 (met) to about 83 (pro) and from about 89 (pro) to about 165 (gly). The putative polypeptide sequence comprises four cysteine residues which are not characteristic of a human ubiquitin domain, e.g., that of UCRP of Narasimhan, et al. (1996) J. Biol. Chem. 271:324–330. Note the ubiquitin conserved residues 48 (lys) and 70 (lys) are present here, which residues have been implicated in protein binding. The terminal glycine doublet is also characteristic. See SEQ ID NO: 1 and 2. This sequence was derived from an activated CD1a dendritic cell library.

```
CTT ACC CTG AAA GTG GTG AAG CCC AGT GAT GAG GAG CTG CCC TTG TTT      291
Leu Thr Leu Lys Val Val Lys Pro Ser Asp Glu Glu Leu Pro Leu Phe
            80                  85                  90

CTT GTG GAG TCA GGT GAT GAG GCA AAG AGG CAC CTC CTC CAG GTG CGA      339
Leu Val Glu Ser Gly Asp Glu Ala Lys Arg His Leu Leu Gln Val Arg
                95                  100                 105

AGG TCC AGC TCA GTG GCA CAA GTG AAA GCA ATG ATC GAG ACT AAG ACG      387
Arg Ser Ser Ser Val Ala Gln Val Lys Ala Met Ile Glu Thr Lys Thr
                110                 115                 120

GGT ATA ATC CCT GAG ACC CAG ATT GTG ACT TGC AAT GGA AAG AGA CTG      435
Gly Ile Ile Pro Glu Thr Gln Ile Val Thr Cys Asn Gly Lys Arg Leu
        125                 130                 135

GAA GAT GGG AAG ATG ATG GCA GAT TAC GGC ATC AGA AAG GGC AAC TTA      483
Glu Asp Gly Lys Met Met Ala Asp Tyr Gly Ile Arg Lys Gly Asn Leu
140                 145                 150                 155

CTC TTC CTG GCA TCT TAT TGT ATT GGA GGG TGACCACCCT GGGGATGGGG        533
Leu Phe Leu Ala Ser Tyr Cys Ile Gly Gly
                160                 165

TGTTGGCAGG GGTCAAAAAG CTTATTTCTT TTAATCTCTT ACTCAACGAA CACATCTTCT    593

GATGATTTCC CAAAATTAAT GAGAATGAGA TGAGTAGAGT AAGATTTGGG TGGGATGGGT    653

AGGATGAAGT ATATTGCCCA ACTCTATGTT TCTTTGATTC TAACACAATT AATTAAGTGA    713

CATGATTTTT ACTAATGTAT TACTGAGACT AGTAAATAAA TTTTTAAGGC AAAATAGAGC    773

ATTC                                                                 777
``` counterpart mouse DU gene (SEQ ID NO: 3 and 4):
```
TACAGAC ATG GCT TCT GTC CGC ACC TGT GTT GTC CGT TCA GAC CAA TGG       49
        Met Ala Ser Val Arg Thr Cys Val Val Arg Ser Asp Gln Trp
          1                 5                  10

CGG TAA ATG ACC TTT GAG ACC ACT GAG AAT GAC AAA GTG AAG AAG ATA       97
Arg Leu Met Thr Phe Glu Thr Thr Glu Asn Asp Lys Val Lys Lys Ile
 15                  20                  25                  30

AAT GAA CAT ATT AGG TCC CAA ACC AAG GTC TCT GTA CAG GAC CAG ATC      145
Asn Glu His Ile Arg Ser Gln Thr Lys Val Ser Val Gln Asp Gln Ile
                35                  40                  45

CTT CTG CTA GAC TCC AAA ATC CTC AAG CCC CAT CGA AAA TTG TCA TCC      193
Leu Leu Leu Asp Ser Lys Ile Leu Lys Pro His Arg Lys Leu Ser Ser
            50                  55                  60

TAT GGG ATT GAC AAG GAA ACC ACT ATC CAC CTT ACC CTG AAG GTG GTG      241
Tyr Gly Ile Asp Lys Glu Thr Thr Ile His Leu Thr Leu Lys Val Val
            65                  70                  75

AAG CCC AGT GAT GAA GAG CTG CCC TTG TTT CTG GTG GAG TCC AAA AAC      289
Lys Pro Ser Asp Glu Glu Leu Pro Leu Phe Leu Val Glu Ser Lys Asn
        80                  85                  90

GAG GGG CAA AGG CAC CTC CTC CGA GTT CGA AGA TCC AGC TCA GTG GCC      337
Glu Gly Gln Arg His Leu Leu Arg Val Arg Arg Ser Ser Ser Val Ala
 95                 100                 105                 110

CAG GTG AAA GAG ATG ATC GAG AGT GTG ACC TCT GTG ATC CCT AAG AAG      385
Gln Val Lys Glu Met Ile Glu Ser Val Thr Ser Val Ile Pro Lys Lys
                115                 120                 125
```

TABLE 1-continued

Sequence encoding a humnan di-ubiquitin protein, containing two ubiquitin domains which extend from about 1 (met) to about 83 (pro) and from about 89 (pro) to about 165 (gly). The putative polypeptide sequence comprises four cysteine residues which are not characteristic of a human ubiquitin domain, e.g., that of UCRP of Narasimhan, et al. (1996) J. Biol. Chem. 271:324–330. Note the ubiquitin conserved residues 48 (lys) and 70 (lys) are present here, which residues have been implicated in protein binding. The terminal glycine doublet is also characteristic. See SEQ ID NO: 1 and 2. This sequence was derived from an activated CD1a dendritic cell library.

```
CAG GTT GTG AAT TGC AAC GGA AAG AAG CTG GAA GAT GGA AAG ATC ATG    433
Gln Val Val Asn Cys Asn Gly Lys Lys Leu Glu Asp Gly Lys Ile Met
            130             135                 140

GCT GAC TAC AAC ATC AAG AGT GGC AGT TTG CTC TTT CTG ACA ACA CAC    481
Ala Asp Tyr Asn Ile Lys Ser Gly Ser Leu Leu Phe Leu Thr Thr His
        145                 150                 155

TGC ACT GGG GGA TGA                                                 496
Cys Thr Gly Gly
        160 comparison of human and mouse diubiquitin polypeptide sequences:
hDU   1    MAPNASCLCVHVRSEEWDLMTFDANPYDSVKKIKEHVRSKTKVPVQDQVL    50
mDU        MASVRTCV---VRSDQWRLMTFETTENDKVKKINEHIRSQTKVSVQDQIL    47
           **  .*.  ***..* ****... * ** ..* ****.* hDU  51    LLGSKILKPRRSLSSYGIDKEKTIHLTLKVVKPSDEELPLFLVESGDEAK   100
mDU  48    LLDSKILKPHRKLSSYGIDKETTIHLTLKVVKPSDEELPLFLVESKNEGQ    97
           ** ******.* ********* ********************** * .

hDU 101    RHLLQVRRSSSVAQVKAMIETKTGIIPETQIVTCNGKRLEDGKMMADYGI   150
mDU  98    RHLLRVRRSSSVAQVKEMIESVTSVIPKKQVVNCNGKKLEDGKIMADYNI   147
           **.****** *.* .** .*.**.*** *.****.* hDU 151    RKGNLLFLASYCIGG                                     165
mDU 148    KSGSLLFLTTHCTGG                                     162
           . * ****.. * **
```

TABLE 2

Sequence encoding a protein related to Ig family members, designated A07C03, isolated froM an activated CD1a dendritic cell library. At about positions 578 and 710, various isolates have various insertions/deletions which suggest positions of intron splicing. A putative signal sequence may run from about -22 (met) to about -1 (val), and a potential transmembrane segment runs from about 132 (phe) to about 154 (leu). Certain cysteine residues, e.g., at positions 29 and 96 are characteristic of Ig domains. A region similar to the J chain of a type 1 variable chain runs from about 112 (gly) to about 119 (val). Two putative glycosylation sites are found in the part amino proximal to the transmembrane portion, with various putative phosphorylation sites in the carboxy proximal part. See SEQ ID NO: 5 and 6. Sequence analysis suggests A07C03 is a member of the Ig superfamily of receptors, and is closely related to the CD8 family, which contain a V1J-type fold. A mouse counterpart is probably encoded in the EST W55567.

```
TTCCTTTCAA ATACACACCC CAACCCGCCC CGGCATACAC AGAA ATG GGG ACT GCG     56
                                                 Met Gly Thr Ala
                                                 -22     -20

AGC AGA AGC AAC ATC GCT CGC CAT CTG CAA ACC AAT CTC ATT CTA TTT    104
Ser Arg Ser Asn Ile Ala Arg His Leu Gln Thr Asn Leu Ile Leu Phe
        -15             -10                  -5

TGT GTC GGT GCT GTG GGC GCC TGT ACT CTC TCT GTC ACA CAA CCG TGG   152
Cys Val Gly Ala Val Gly Ala Cys Thr Leu Ser Val Thr Gln Pro Trp
         1               5                 10

TAC CTA GAA GTG GAC TAC ACT CAT GAG GCC GTC ACC ATA AAG TGT ACC   200
Tyr Leu Glu Val Asp Tyr Thr His Glu Ala Val Thr Ile Lys Cys Thr
 15              20                 25                 30
```

TABLE 2-continued

Sequence encoding a protein related to Ig family members, designated A07C03, isolated froM an activated CD1a dendritic cell library. At about positions 578 and 710, various isolates have various insertions/deletions which suggest positions of intron splicing. A putative signal sequence may run from about -22 (met) to about -1 (val), and a potential transmembrane segment runs from about 132 (phe) to about 154 (leu). Certain cysteine residues, e.g., at positions 29 and 96 are characteristic of Ig domains. A region similar to the J chain of a type 1 variable chain runs from about 112 (gly) to about 119 (val). Two putative glycosylation sites are found in the part amino proximal to the transmembrane portion, with various putative phosphorylation sites in the carboxy proximal part. See SEQ ID NO: 5 and 6. Sequence analysis suggests A07C03 is a member of the Ig superfamily of receptors, and is closely related to the CD8 family, which contain a V1J-type fold. A mouse counterpart is probably encoded in the EST W55567.

```
TTC TCC GCA ACC GGA TGC CCT TCT GAG CAA CCA ACA TGC CTG TGG TTT    248
Phe Ser Ala Thr Gly Cys Pro Ser Glu Gln Pro Thr Cys Leu Trp Phe
            35                  40                  45

CGC TAC GGT GCT CAC CAG CCT GAG AAC CTG TGC TTG GAC GGG TGC AAA    296
Arg Tyr Gly Ala His Gln Pro Glu Asn Leu Cys Leu Asp Gly Cys Lys
        50                  55                  60

AGT GAG GCA GAC AAG TTC ACA GTG AGG GAG GCC CTC AAA GAA AAC CAA    344
Ser Glu Ala Asp Lys Phe Thr Val Arg Glu Ala Leu Lys Glu Asn Gln
        65                  70                  75

GTT TCC CTC ACT GTA AAC AGA GTG ACT TCA AAT GAC AGT GCA ATT TAC    392
Val Ser Leu Thr Val Asn Arg Val Thr Ser Asn Asp Ser Ala Ile Tyr
    80                  85                  90

ATC TGT GGA ATA GCA TTC CCC AGT GTG CCG GAA GCG AGA GCT AAA CAG    440
Ile Cys Gly Ile Ala Phe Pro Ser Val Pro Glu Ala Arg Ala Lys Gln
 95                 100                 105                 110

ACA GGA GGA GGG ACC ACA CTG GTG GTA AGA GAA ATT AAG CTG CTC AGC    488
Thr Gly Gly Gly Thr Thr Leu Val Val Arg Glu Ile Lys Leu Leu Ser
                115                 120                 125

AAG GAA CTG CGG AGC TTC CTG ACA GCT CTT GTQ TCA CTG CTC TTC GTC    536
Lys Glu Leu Arg Ser Phe Leu Thr Ala Leu Val Ser Leu Leu Ser Val
        130                 135                 140

TAT GTG ACC GGT GTG TGC GTG GCC TTC ATA CTC CTC TCC AAA TCA AAA    584
Tyr Val Thr Gly Val Cys Val Ala Phe Ile Leu Leu Ser Lys Ser Lys
        145                 150                 155

TCC AAC CCT CTA AGA AAG AAA GAA ATA AAA GAA GAC TCA CAA AAG AAG    632
Ser Asn Pro Leu Arg Lys Lys Glu Ile Lys Glu Asp Ser Gln Lys Lys
    160                 165                 170

AAG AGT GCT CGG CGT ATT TTT CAG GAA ATT GCT CAA GAA CTA TAC CAT    680
Lys Ser Ala Arg Arg Ile Phe Gln Glu Ile Ala Gln Glu Leu Tyr His
175                 180                 185                 190

AAG AGA CAT GTG GAA ACA AAT CAG CAA TCT GAG AAA GAT AAC AAC ACT    728
Lys Arg His Val Glu Thr Asn Gln Gln Ser Glu Lys Asp Asn Asn Thr
                195                 200                 205

TAT GAA AAC AGA AGA GTA CTT TCC AAC TAT GAA AGG CCA TAGAAACGTT    777
Tyr Glu Asn Arg Arg Val Leu Ser Asn Tyr Glu Arg Pro
                210                 215

TTAATTTTCA ATGAAGTCAC TGAAAATCCA ACTCCAGGAG CTATGGCAGT GTTAATGAAC    837

ATATATCATC AGGTCTTAAA AAAAAAATAA AGGTAAACTG AAAAGACAAC TGGCTACAAA    897

GAAGGATGTC AGAATGTAAG GAAACTATAA CTAATAGTCA TTACCAAAAT ACTAAAACCC    957

AACAAAATGC AACTGAAAAA TACCTTCCAA ATTTGCCAAG AAAAAAAATT CTATTAAACT   1017

AAAAAAAAAA AAAAAAAAAA AAA                                          1040 improved human sequence (SEQ ID NO: 7 and 8):
TTCCTTTCAA ATACACACCC CAACCCGCCC CGGCATATAC AGAA ATG GGG ACT GCG     56
                                              Met Gly Thr Ala
                                              -22     -20
```

TABLE 2-continued

Sequence encoding a protein related to Ig family members, designated A07C03, isolated froM an activated CD1a dendritic cell library. At about positions 578 and 710, various isolates have various insertions/deletions which suggest positions of intron splicing. A putative signal sequence may run from about -22 (met) to about -1 (val), and a potential transmembrane segment runs from about 132 (phe) to about 154 (leu). Certain cysteine residues, e.g., at positions 29 and 96 are characteristic of Ig domains. A region similar to the J chain of a type 1 variable chain runs from about 112 (gly) to about 119 (val). Two putative glycosylation sites are found in the part amino proximal to the transmembrane portion, with various putative phosphorylation sites in the carboxy proximal part. See SEQ ID NO: 5 and 6. Sequence analysis suggests A07C03 is a member of the Ig superfamily of receptors, and is closely related to the CD8 family, which contain a V1J-type fold. A mouse counterpart is probably encoded in the EST W55567.

```
AGC AGA AGC AAC ATC GCT CGC CAT CTG CAA ACC AAT CTC ATT CTA TTT    104
Ser Arg Ser Asn Ile Ala Arg His Leu Gln Thr Asn Leu Ile Leu Phe
            -15             -10                 -5

TGT GTC GGT GCT GTG GGC GCC TGT ACT CTC TCT GTC ACA CAA CCG TGG    152
Cys Val Gly Ala Val Gly Ala Cys Thr Leu Ser Val Thr Gln Pro Trp
             1               5                  10

TAC CTA GAA GTG GAC TAC ACT CAT GAG GCC GTC ACC ATA AAG TGT ACC    200
Tyr Leu Glu Val Asp Tyr Thr His Glu Ala Val Thr Ile Lys Cys Thr
 15              20                  25                  30

TTC TCC GCA ACC GGA TGC CCT TCT GAG CAA CCA ACA TGC CTG TGG TTT    248
Phe Ser Ala Thr Gly Cys Pro Ser Glu Gln Pro Thr Cys Leu Trp Phe
                 35                  40                  45

CGC TAC GGT GCT CAC CAG CCT GAG AAC CTG TGC TTG GAC GGG TGC AAA    296
Arg Tyr Gly Ala His Gln Pro Glu Asn Leu Cys Leu Asp Gly Cys Lys
             50                  55                  60

AGT GAG GCA GAC AAG TTC ACA GTG AGG GAG GCC CTC AAA GAA AAC CAA    344
Ser Glu Ala Asp Lys Phe Thr Val Arg Glu Ala Leu Lys Glu Asn Gln
         65                  70                  75

GTT TCC CTC ACT GTA AAC AGA GTG ACT TCA AAT GAC AGT GCA ATT TAC    392
Val Ser Leu Thr Val Asn Arg Val Thr Ser Asn Asp Ser Ala Ile Tyr
     80                  85                  90

ATC TGT GGA ATA GCA TTC CCC AGT GTG CCG GAA GCG AGA GCT AAA CAG    440
Ile Cys Gly Ile Ala Phe Pro Ser Val Pro Glu Ala Arg Ala Lys Gln
 95                  100                 105                 110

ACA GGA GGA GGG ACC ACA CTG GTG GTA AGA GAA ATT AAG CTG CTC AGC    488
Thr Gly Gly Gly Thr Thr Leu Val Val Arg Glu Ile Lys Leu Leu Ser
                 115                 120                 125

AAG GAA CTG CGG AGC TTC CTG ACA GCT CTT GTA TCA CTG CTC TCT GTC    536
Lys Glu Leu Arg Ser Phe Leu Thr Ala Leu Val Ser Leu Leu Ser Val
             130                 135                 140

TAT GTG ACC GGT GTG TGC GTG GCC TTC ATA CTC CTC TCC AAA TCA AAA    584
Tyr Val Thr Gly Val Cys Val Ala Phe Ile Leu Leu Ser Lys Ser Lys
         145                 150                 155

TCC AAC CCT CTA AGA AAG AAA GAA ATA AAA GAA GAC TCA CAA AAG AAG    632
Ser Asn Pro Leu Arg Lys Lys Glu Ile Lys Glu Asp Ser Gln Lys Lys
     160                 165                 170

AAG AGT GCT CGG CGT ATT TTT CAG GAA ATT GCT CAA GAA CTA TAC CAT    680
Lys Ser Ala Arg Arg Ile Phe Gln Glu Ile Ala Gln Glu Leu Tyr His
175                 180                 185                 190

AAG AGA CAT GTG GAA ACA AAT CAG CAA TCT GAG AAA GAT AAC AAC ACT    728
Lys Arg His Val Glu Thr Asn Gln Gln Ser Glu Lys Asp Asn Asn Thr
                 195                 200                 205

TAT GAA AAC AGA AGA GTA CTT TCC AAC TAT GAA AGG CCA TAGAAACGTT     777
Tyr Glu Asn Arg Arg Val Leu Ser Asn Tyr Glu Arg Pro
             210                 215
```

TABLE 2-continued

Sequence encoding a protein related to Ig family members, designated A07C03, isolated froM an activated CD1a dendritic cell library. At about positions 578 and 710, various isolates have various insertions/deletions which suggest positions of intron splicing. A putative signal sequence may run from about -22 (met) to about -1 (val), and a potential transmembrane segment runs from about 132 (phe) to about 154 (leu). Certain cysteine residues, e.g., at positions 29 and 96 are characteristic of Ig domains. A region similar to the J chain of a type 1 variable chain runs from about 112 (gly) to about 119 (val). Two putative glycosylation sites are found in the part amino proximal to the transmembrane portion, with various putative phosphorylation sites in the carboxy proximal part. See SEQ ID NO: 5 and 6. Sequence analysis suggests A07C03 is a member of the Ig superfamily of receptors, and is closely related to the CD8 family, which contain a V1J-type fold. A mouse counterpart is probably encoded in the EST W55567.

```
TTAATTTTCA ATGAAGTCAC TGAAAATCCA ACTCCAGGAG CTATGGCAGT GTTAATGAAC    837

ATATATCATC AGGTCTTAAA AAAAAAATAA AGGTAAACTG AAAAGACAAC TGGCTACAAA    897

GAAGGATGTC AGAATGTAAG GAAACTATAA CTAATAGTCA TTACCAAAAT ACTAAAACCC    957

AACAAAATGC AACTGAAAAA TACCTTCCAA ATTTGCCAAG AAAAAAAATT CTATTCCAAA   1017

CTAAAAAAAA AAAAAAAAA AAAAA                                         1042 counterpart mouse A07C03 (SEQ ID NO: 9 and 10)
CCACGCGTCC GGGAAAAGGC GGCACTGCA CCAGCG ATG GGC CCT GTG AGC ACG        54
                                    Met Gly Pro Val Ser Thr
                                    -22         -20

AGC AGG AGG GGC CTC CGG CTA GGA ATC AGC CTG ATC CTT CTT CAA GTT      102
Ser Arg Arg Gly Leu Arg Leu Gly Ile Ser Leu Ile Leu Leu Gln Val
    -15              -10                  -5

GGT GTG GTG GGC GCC TGT ACT GTA TCT GTG CTA CAG CCA GGT TAC CTA      150
Gla Val Val Gly Ala Cys Thr Val Ser Val Leu Gln Pro Gly Tyr Leu
 1               5                   10                  15

GAG GTG GAC TAC ACG TCT CAG ACT GTC ACC ATG GAG TGT ACC TTT TCT      198
Glu Val Asp Tyr Thr Ser Gln Thr Val Thr Met Glu Cys Thr Phe Ser
             20                  25                  30

ACA ACT GGA TGC CCT GCA GTG CAA CCA AAA AGC TTG TGG TTT CGC TGT      246
Thr Thr Gly Cys Pro Ala Val Gln Pro Lys Ser Leu Trp Phe Arg Cys
         35                  40                  45

GGC ACT CAC CAG CCT GAA GCT CTG TGC TTG GAC GGA TGC AGA AAT GAG      294
Gly Thr His Gln Pro Glu Ala Leu Cys Leu Asp Gly Cys Arg Asn Glu
     50                  55                  60

GCA GAC AAG TTC ACA GTG AAA GAA ACC CTG GAC CAG AAC CGA GTC TCC      342
Ala Asp Lys Phe Thr Val Lys Glu Thr Leu Asp Gln Asn Arg Val Ser
 65              70                  75                  80

CTC ACT GTT AAC AGG CTG TCT CCA AAT GAC AGT GCA ATC TAC ATC TGT      390
Leu Thr Val Asn Arg Leu Ser Pro Asn Asp Ser Ala Ile Tyr Ile Cys
             85                  90                  95

GGA ATA GCA TTT CCC AAT GAA CCG GTA CCA ACA GCC AAA CAG ACT GGA      438
Gly Ile Ala Phe Pro Asn Glu Pro Val Pro Thr Ala Lys Gln Thr Gly
         100                 105                 110

GAC GGG ACT ACA CTG GTG GTA AGA GAA AGA CTT TTC AGC AGG GAG GTG      486
Asp Gly Thr Thr Leu Val Val Arg Glu Arg Leu Phe Ser Arg Glu Val
     115                 120                 125

CAC AGT CTC CTG ATA GTG CTC TTA GCA CTG CTC GCA GTC TAC GTC ACC      534
His Ser Leu Leu Ile Val Leu leu Ala Leu Leu Ala Val Tyr Val Thr
 130                 135                 140

GGT GTG TGT GTG ATC TTC ATA GTC CTC TTC AGA TCA AAA TCT AAC ACT      582
Gly Val Cys Val Ile Phe Ile Val Leu Phe Arg Ser Lys Ser Asn Thr
145                  150                 155                 160

CCA AGA AGC AGA GAA ACC AAG GAA GAC TCG AAA AAG AAG AGT GCT CGA      630
Pro Arg Ser Arg Glu Thr Lys Glu Asp Ser Lys Lys Lys Ser Ala Arg
             165                 170                 175
```

TABLE 2-continued

Sequence encoding a protein related to Ig family members, designated A07C03, isolated froM an activated CD1a dendritic cell library. At about positions 578 and 710, various isolates have various insertions/deletions which suggest positions of intron splicing. A putative signal sequence may run from about -22 (met) to about -1 (val), and a potential transmembrane segment runs from about 132 (phe) to about 154 (leu). Certain cysteine residues, e.g., at positions 29 and 96 are characteristic of Ig domains. A region similar to the J chain of a type 1 variable chain runs from about 112 (gly) to about 119 (val). Two putative glycosylation sites are found in the part amino proximal to the transmembrane portion, with various putative phosphorylation sites in the carboxy proximal part. See SEQ ID NO: 5 and 6. Sequence analysis suggests A07C03 is a member of the Ig superfamily of receptors, and is closely related to the CD8 family, which contain a V1J-type fold. A mouse counterpart is probably encoded in the EST W55567.

```
CGT ATC TTC CAG GAA ATT GCT CAA GAA TTA TAC CAT AAG AGA TAT GTG     678
Arg Ile Phe Gln Glu Ile Ala Gln Glu Leu Tyr His Lys Arg Tyr Val
            180                 185                 190

GAA ACA AGT CAT CAG CCT GAG CAA GAC GGC AAT TAT GAA AAC AGA AAA     726
Glu Thr Ser His Gln Pro Glu Gln Asp Gly Asn Tyr Glu Asn Arg Lys
            195                 200                 205

GCA CTC CCC AGC CCT GGA AGA CCA TAGATGTGCT GACTTTTTAC TTAAACCATT    780
Ala Leu Pro Ser Pro Gly Arg Pro
    210                 215

GACAGTGCAA CTCCAGAATC TATGGCAGTG TGAATGGACA TACAGCAATC CAAACAACAG   840

CAAAGAGAGC TGAGGTGTAG CTTGAGTGGC AAAGTGCTTG CCCAGTAGGC ATGAAGTCTT   900

AGCTTTGATC CTCAGCACCA CATAACTCAG CAAAGTGACA CAAGCCTGTA TTCCCAACAT   960

TGTGTAGTAG TATAAAAAGT CAGAAGTTCA AGGTCATCCC TGACTATAGG ATGAACCTGA  1020

AGTCAGAGAC ATGTTATCTT GTCTCAAAAA CACTGCCACC ACCAAGAGAA AAGGGCAGGA  1080

CAAGTGGGAA AACAGCCAGT CACGCCAGAA GGCAGAGCGG AAGTAACTGT CACGAACCAT  1140

AATGATGGAA TGTGAAAACC TCAAGAAAAC TCAACTGGAG GACCTTTTTT CTAATTTTCC  1200

AGGAACAGTC TAAGGAGCCT CATTTTAAAG AAAAACTTCA CCTTCAGCTT TTA         1253
```

Comparison of human and mouse protein sequences:
```
    human    MG...TASRS NIARHLQTNL ILFCVGAVGA CTLSVTQPWY LEVDYTHEAV
    mouse    MGPVST.SRR GL.R.LGISL ILLQVGVVGA CTVSVLQPGY LEVDYTSQTV human    TIKCTFSATG CPSEQPTCLW FRYGAHQPEN LCLDGCKSEA DKFTVREALK
    mouse    TMECTFSTTG CPAVQPKSLW FRCGTHQPEA LCLDGCRNEA DKFTVKETLD human    ENQVSLTVNR VTSNDSAIYI CGIAFPS..V PEARAKQTGG GTTLVVREIK
    mouse    QNRVSLTVNR LSPNDSAIYI CGIAFPNEKV P..TAKQTGD GTTLVVRE.R human    LLSKELRSFL TALVSLLSVY VTGVCVAFIL LSKSKSN.PL RKKEIKEDSQ
    mouse    LFSREVHSLL IVLLALLAVY VTGVCVIFIV LFRSKSNTP. RSRETKEDS.

human    KKKSARRIFQ EIAQELYHKR HVETNQQSEK DNNTYENRRV LSNYERP
    mouse    KKKSARRIFQ EIAQELYHKR YVETSHQPEQ DGN.YENRKA LPSPGRP
```

TABLE 3

Sequence encoding a protein related to LAMP-like family members, designated E02B02, isolated from human CD1a dendritic cells. The encoded protein exhibits homology to Lysosome-Associated Membrane Protein (LAMP) family, see human LMP1 and LMP2 and CD68. Notable features are a hydrophobic length from about -23 (met) to about -1 (ser), putatively a signal sequence; a putative transmembrane segment from about ile359 to leu383; and a serine/proline rich stretch suggestive of a hinge from about pro184 to ser199. The sequence also exhibits presumptive glycosylation sites, intracellular tyrosine. See SEQ ID NO: 11 and 12.

```
CCCCCGGCCA GGTAGCGGCC GCTGAATTCT AGAACGCCCA CC ATG CCC CGC CAG       54
                                                Met Pro Arg Gln
                                                -23         -20
```

TABLE 3-continued

Sequence encoding a protein related to LAMP-like family members, designated E02B02, isolated from human CD1a dendritic cells. The encoded protein exhibits homology to Lysosome-Associated Membrane Protein (LAMP) family, see human LMP1 and LMP2 and CD68. Notable features are a hydrophobic length from about −23 (met) to about −1 (ser), putatively a signal sequence; a putative transmembrane segment from about ile359 to leu383; and a serine/proline rich stretch suggestive of a hinge from about pro184 to ser199. The sequence also exhibits presumptive glycosylation sites, intracellular tyrosine. See SEQ ID NO: 11 and 12.

| | | | | | | | | | | | | | | |
|---|---|---|---|---|---|---|---|---|---|---|---|---|---|---|
| CTC | ACC | GCG | GCG | GCC | GCG | CTC | TTC | GCG | TCC | CTG | CCC | GTA | ATT | TTG | CAC | 102 |
| Leu | Ser | Ala | Ala | Ala | Ala | Leu | Phe | Ala | Ser | Leu | Ala | Val | Ile | Leu | His |
| | | | −15 | | | | −10 | | | | | −5 | | | |
| GAT | GGC | AGT | CAA | ATG | AGA | GCA | AAA | GCA | TTT | CCA | GAA | ACC | AGA | GAT | TAT | 150 |
| Asp | Gly | Ser | Gln | Met | Arg | Ala | Lys | Ala | Phe | Pro | Glu | Thr | Arg | Asp | Tyr |
| | | | | 1 | | | | 5 | | | | | 10 | | |
| TCT | CAA | CCT | ACT | GCA | GCA | GCA | ACA | GTA | CAC | GAC | ATA | AAA | AAA | CCT | GTC | 198 |
| Ser | Gln | Pro | Thr | Ala | Ala | Ala | Thr | Val | Gln | Asp | Ile | Lys | Lys | Pro | Val |
| | 15 | | | | | 20 | | | | | 25 | | | | |
| CAG | CAA | CCA | GCT | AAG | CAA | GCA | CCT | CAC | CAA | ACT | TTA | GCA | GCA | AGA | TTC | 246 |
| Gln | Gln | Pro | Ala | Lys | Gln | Ala | Pro | His | Gln | Thr | Leu | Ala | Ala | Arg | Phe |
| | 30 | | | | 35 | | | | | 40 | | | | | 45 |
| ATC | GAT | GGT | CAT | ATC | ACC | TTT | CAA | ACA | GCG | GCC | ACA | GTA | AAA | ATT | CCA | 294 |
| Met | Asp | Gly | His | Ile | Thr | Phe | Gln | Thr | Ala | Ala | Thr | Val | Lys | Ile | Pro |
| | | | | 50 | | | | | 55 | | | | | 60 | |
| ACA | ACT | ACC | CCA | GCA | ACT | ACA | AAA | AAC | ACT | GCA | ACC | ACC | AGC | CCA | ATT | 342 |
| Thr | Thr | Thr | Pro | Ala | Thr | Thr | Lys | Asn | Thr | Ala | Thr | Thr | Ser | Pro | Ile |
| | | | 65 | | | | | 70 | | | | | 75 | | |
| ACC | TAC | ACC | CTG | GTC | ACA | ACC | CAG | GCC | ACA | CCC | AAC | AAC | TCA | CAC | ACA | 390 |
| Thr | Tyr | Thr | Leu | Val | Thr | Thr | Gln | Ala | Thr | Pro | Asn | Asn | Ser | His | Thr |
| | | | 80 | | | | | 85 | | | | | 90 | | |
| GCT | CCT | CCA | GTT | ACT | GAA | GTT | ACA | GTC | GGC | CCT | AGC | TTA | GCC | CCT | TAT | 438 |
| Ala | Pro | Pro | Val | Thr | Glu | Val | Thr | Val | Gly | Pro | Ser | Leu | Ala | Pro | Tyr |
| | | 95 | | | | | 100 | | | | | 105 | | | |
| TCA | CTG | CCA | CCC | ACC | ATC | ACC | CCA | CCA | GCT | CAT | ACA | ACT | GGA | ACC | AGT | 486 |
| Ser | Leu | Pro | Pro | Thr | Ile | Thr | Pro | Pro | Ala | His | Thr | Thr | Gly | Thr | Ser |
| 110 | | | | | 115 | | | | | 120 | | | | | 125 |
| TCA | TCA | ACC | GTC | AGC | CAC | ACA | ACT | GGG | AAC | ACC | ACT | CAA | CCC | AGT | AAC | 534 |
| Ser | Ser | Thr | Val | Ser | His | Thr | Thr | Gly | Asn | Thr | Thr | Gln | Pro | Ser | Asn |
| | | | | 130 | | | | | 135 | | | | | 140 | |
| CAG | ACC | ACC | CTT | CCA | GCA | ACT | TTA | TCG | ATA | GCA | CTG | CAC | AAA | AGC | ACA | 582 |
| Gln | Thr | Thr | Leu | Pro | Ala | Thr | Leu | Ser | Ile | Ala | Leu | His | Lys | Ser | Thr |
| | | | 145 | | | | | 150 | | | | | 155 | | |
| ACC | GGT | CAG | AAG | CCT | GTT | CAA | CCC | ACC | CAT | GCC | CCA | GGA | ACA | ACG | GCA | 630 |
| Thr | Gly | Gln | Lys | Pro | Val | Gln | Pro | Thr | His | Ala | Pro | Gly | Thr | Thr | Ala |
| | | | 160 | | | | | 165 | | | | | 170 | | |
| GCT | GCC | CAC | AAT | ACC | ACC | CGC | ACA | GCT | GCA | CCT | GCC | TCC | ACG | GTT | CCT | 678 |
| Ala | Ala | His | Asn | Thr | Thr | Arg | Thr | Ala | Ala | Pro | Ala | Ser | Thr | Val | Pro |
| | | | 175 | | | | | 180 | | | | | 185 | | |
| GGG | CCC | ACC | CTT | GCA | CCT | CAG | CCA | TCG | TCA | GTC | AAG | ACT | GGA | ATT | TAT | 726 |
| Gly | Pro | Thr | Leu | Ala | Pro | Gln | Pro | Ser | Ser | Val | Lys | Thr | Gly | Ile | Tyr |
| 190 | | | | | 195 | | | | | 200 | | | | | 205 |
| CAG | GTT | CTA | AAC | GGA | AGC | AGA | CTC | TGT | ATA | AAA | GCA | GAG | ATG | GGG | ATA | 774 |
| Gln | Val | Leu | Asn | Gly | Ser | Arg | Leu | Cys | Ile | Lys | Ala | Glu | Met | Gly | Ile |
| | | | | 210 | | | | | 215 | | | | | 220 | |
| CAG | CTG | ATT | GTT | CAA | GAC | AAG | GAG | TCG | GTT | TTT | TCA | CCT | CGG | AGA | TAC | 822 |
| Gln | Leu | Ile | Val | Gln | Asp | Lys | Glu | Ser | Val | Phe | Ser | Pro | Arg | Arg | Tyr |
| | | | | 225 | | | | | 230 | | | | | 235 | |
| TTC | AAC | ATC | GAC | CCC | AAC | GCA | ACG | CAA | GCC | TCT | GGG | AAC | TGT | GGC | ACC | 870 |
| Phe | Asn | Ile | Asp | Pro | Asn | Ala | Thr | Gln | Ala | Ser | Gly | Asn | Cys | Gly | Thr |
| | | | 240 | | | | | 245 | | | | | 250 | | |

TABLE 3-continued

Sequence encoding a protein related to LAMP-like family members, designated E02B02, isolated from human CD1a dendritic cells. The encoded protein exhibits homology to Lysosome-Associated Membrane Protein (LAMP) family, see human LMP1 and LMP2 and CD68. Notable features are a hydrophobic length from about −23 (met) to about −1 (ser), putatively a signal sequence; a putative transmembrane segment from about ile359 to leu383; and a serine/proline rich stretch suggestive of a hinge from about pro184 to ser199. The sequence also exhibits presumptive glycosylation sites, intracellular tyrosine. See SEQ ID NO: 11 and 12.

```
CGA AAA TCC AAC CTT CTG TTG AAT TTT CAG GGC GGA TTT GTG AAT CTC    918
Arg Lys Ser Asn Leu Leu Leu Asn Phe Gln Gly Gly Phe Val Asn Leu
    255             260                 265

ACA TTT ACC AAG GAT GAA GAA TCA TAT TAT ATC AGT GAA GTG GGA GCC    966
Thr Phe Thr Lys Asp Glu Glu Ser Tyr Tyr Ile Ser Glu Val Gly Ala
270             275                 280                 285

TAT TTG ACC GTC TCA GAT CCA GAG ACA ATT TAC CAA GGA ATC AAA CAT   1014
Tyr Leu Thr Val Ser Asp Pro Glu Thr Ile Tyr Gln Gly Ile Lys His
                290                 295                 300

GCG GTG GTG ATG TTC CAG ACA GCA GTC GGG CAT TCC TTC AAG TGC GTG   1062
Ala Val Val Met Phe Gln Thr Ala Val Gly his Ser Phe Lys Cys Val
            305                 310                 315

AGT GAA CAG AGC CTC CAG TTG TCA GCC CAC CTG CAG GTG AAA ACA ACC   1110
Ser Glu Gln Ser Leu Gln Leu Ser Ala His Leu Gln Val Lys Thr Thr
        320                 325                 330

GAT GTC CAA CTT CAA GCC TTT GAT TTT GAA GAT GAC CAC TTT GGA AAT   1158
Asp Val Gln Leu Gln Ala Phe Asp Phe Glu Asp Asp His Phe Gly Asn
    335                 340                 345

GTG GAT GAG TGC TCG TCT GAC TAC ACA ATT GTG CTT CCT GTG ATT GGG   1026
Val Asp Glu Cys Ser Ser Asp Tyr Thr Ile Val Leu Pro Val Ile Gly
350                 355                 360                 365

GCC ATC GTG GTT GGT CTC TGC CTT ATG GGT ATG GGT GTC TAT AAA ATC   1254
Ala Ile Val Val Gly Leu Cys Leu Met Gly Met Gly Val Tyr Lys Ile
                370                 375                 380

CGC CTA AGG TGT CAA TCA TCT GGA TAC CAG AGA ATC TAATTGTTGC        1300
Arg Leu Arg Cys Gln Ser Ser Gly Tyr Gln arg Ile
            385                 390

CCGGGGGGAA TGAAAATAAT GGAATTTAGA GAACTCTTTC ATCCTTCCAG GATGGATGTT  1360

GGAAATTCCC TCAGAGTGTG GGTCCTTCAA ACAATGTAAA CCACCATCTT CTATTCAAAT  1420

GAAGTGAGTC ATGTGTGATT TAAGTTCAGG CAGCACATCA ATTTCTAAAT ACTTTTTGTT  1480

TATTTTATGA AAGATATAGT GAGCTGTTTA TTTTCTAGTT TCCTTTAGAA TATTTTAGCC  1540

ACTCAAAGTC AACATTTGAG ATATGTTGAA TTAACATAAT ATATGTAAAG TAGAATAAGC  1600

CTTCAAATTA TAAACCAAGG GTCAATTGTA ACTAATACTA CTGTGTGTGC ATTGAAGATT  1660

TTATTTTACC CTTGATCTTA ACAAAGCCTT TGCTTTGTTA TCAAATGGAC TTTCAGTGCT  1720

TTTACTATCT GTGTTTTATG GTTTCATGTA ACATACATAT TCCTGGTGTA GCACTTAACT  1780

CCTTTTCCAC TTTAAATTTG TTTTTGTTTT TTGAGACGGA GTTTCACTCT TGTCACCCAG  1840

GCTGGAGTAC AGTGGCACGA TCTCGGCTTA TGGCAACCTC CGCCTCCCGG GTTCAAGTGA  1900

TTCTCCTGCT TCAGCTTCCC GAGTAGCTGG GATTACAGGC ACACACTACC ACGCCTGGCT  1960

AATTTTTGTA TTTTTATTAT AGACGGGGTT TCACCATGTT GGCCAGACTG GTCTTGAACT  2020

CTTGACCTCA GGTGATCCAC CCACCTCAGC CTCCCAAAGT GCTGGGATTA CAGGCATGAG  2080

CCATTGCGCC CGGCCTTAAA TGTTTTTTTT AATCATCAAA AAGAACAACA TATCTCAGGT  2140

TGTCTAAGTG TTTTTATGTA AAACCAACAA AAAGAACAAA TCAGCTTATA TTTTTTATCT  2200

TGATGACTCC TGCTCCAGAA TCGCTAGACT AAGAATTAGG TGGCTACAGA TGGTAGAACT  2260
```

TABLE 3-continued

Sequence encoding a protein related to LAMP-like family members, designated E02B02, isolated from human CD1a dendritic cells. The encoded protein exhibits homology to Lysosome-Associated Membrane Protein (LAMP) family, see human LMP1 and LMP2 and CD68. Notable features are a hydrophobic length from about -23 (met) to about -1 (ser), putatively a signal sequence; a putative transmembrane segment from about ile359 to leu383; and a serine/proline rich stretch suggestive of a hinge from about pro184 to ser199. The sequence also exhibits presumptive glycosylation sites, intracellular tyrosine. See SEQ ID NO: 11 and 12.

```
AAACAATAAG CAAGAGACAA TAATAATGGC CCTTAATTAT TAACAAAGTG CCAGAGTCTA   2320

GGCTAAGCAC TTTATCTATA TCTCATTTCA TTCTCACAAC TTATAGGTGA ATGAGTAAAC   2380

TGAGACTTAA GGGAACTGAA TCACTTAAAT GTCACCTGGC TAACTGATGG CAGAGCCAGA   2440

GCTTGAATTC ATGTTGGTCT GACATCAAGG TCTTTGGTCT TCTCCCTACA CCAAGTTACC   2500

TACAAGAACA ATGACACCAC ACTCTGCCTG AAGGCTCACA CCTACATACCA GCATACGCTC   2560

ACCTTACAGG GAAATGGGTT TATCCAGGAT CATGAGACAT TAGGGTAGAT GAAAGGAGAG   2620

CTTTGCAGAT AACAAAATAG CCTATCCTTA ATAAATCCTC CACTCTCTGG AAGGAGACTG   2680

AGGGGCTTTG TAAAACATTA GTCAGTTGCT CATTTTTATG GGATTGCTTA GCTGGGCTGT   2740

AAAGATGAAG GCATCAAATA AACTCAAAGT ATTTTTAAAT TTTTTTGATA ATAGAGAAAC   2800

TTCGCTAACC AACTGTTCTT TCTTGAGTGA TAGCCCCATC TTGTGGTAAC TTGCTGCTTC   2860

TGCACTTCAT ATCCATATTT CCTATTGTTC ACTTTATTCT GTAGAGCAGC CTGCCAAGAA   2920

TTTTATTTCT GCTGTTTTTT TTGCTGCTAA AGAAAGGAAC TAAGTCAGGA TGTTAACAGA   2980

AAAGTCCACA TAACCCTAGA ATTCTTAGTC AAGGAATAAT TCAAGTCAGC CTAGAGACCA   3040

TGTTGACTTT CCTCATGTGT TTCCTTATGA CTCAGTAAGT TGGCAAGGTC CTGACTTTAG   3100

TCTTAATAAA ACATTGAATT GTAGTAAAGG TTTTTGTAAT AAAAACTTAC TTTGGAAAAA   3160

AAAAAAAAAA AA                                                       3172
```

The peptide segments can also be used to produce appropriate oligonucleotides to screen a library to determine the presence of a similar gene, e.g., an identical or polymorphic variant, or to identify a DC. The genetic code can be used to select appropriate oligonucleotides useful as probes for screening. In combination with polymerase chain reaction (PCR) techniques, synthetic oligonucleotides will be useful in selecting desired clones from a library.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding these DC proteins, e.g., subcloning nucleic acid sequences encoding polypeptides into expression vectors, labeling probes, DNA hybridization, and the like are described generally in Sambrook, et al. (1989) *Molecular Cloning—A Laboratory Manual* (2nd ed.) Vol. 1–3, Cold Spring Harbor Laboratory, Cold Spring Harbor Press, NY, which is incorporated herein by reference and hereinafter referred to as "Sambrook, et al." See also, Coligan, et al. (1987 and periodic supplements) *Current Protocols in Molecular Biology* Greene/Wiley, New York, N.Y., referred to as "Coligan, et al."

There are various methods of isolating the DNA sequences encoding these DC proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed with other proteins and selecting specific primers. Such probes can be used directly in hybridization assays to isolate DNA encoding DC proteins, or probes can be designed for use in amplification techniques such as PCR, for the isolation of DNA encoding DC proteins.

To prepare a cDNA library, mRNA is isolated from cells which express the DC protein. cDNA is prepared from the mRNA and ligated into a recombinant vector. The vector is transfected into a recombinant host for propagation, screening and cloning. Methods for making and screening cDNA libraries are well known. See Gubler and Hoffman (1983) *Gene* 25:263–269; Sambrook, et al.; or Coligan, et al.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described, e.g., in Sambrook, et al. or Coligan, et al. Recombinant phage are analyzed by plaque hybridization as described in Benton and Davis (1977) *Science* 196:180–182. Colony hybridization is carried out as generally described in, e.g., Grunstein, et al. (1975) *Proc. Natl. Acad. Sci. USA* 72:3961–3965.

DNA encoding a DC protein can be identified in either cDNA or genomic libraries by its ability to hybridize with the nucleic acid probes described herein, for example in colony or plaque hybridization experiments. The corresponding DNA regions are isolated by standard methods familiar to those of skill in the art. See Sambrook, et al.

Various methods of amplifying target sequences, such as the polymerase chain reaction, can also be used to prepare DNA encoding DC proteins. Polymerase chain reaction (PCR) technology is used to amplify such nucleic acid sequences directly from mRNA, from cDNA, and from genomic libraries or cDNA libraries. The isolated sequences encoding DC proteins may also be used as templates for PCR amplification.

In PCR techniques, oligonucleotide primers complementary to two 5' regions in the DNA region to be amplified are synthesized. The polymerase chain reaction is then carried out using the two primers. See Innis, et al. (eds.) (1990) *PCR Protocols: A Guide to Methods and Applications* Academic Press, San Diego, Calif. Primers can be selected to amplify the entire regions encoding a selected full-length DC protein or to amplify smaller DNA segments as desired. Once such regions are PCR-amplified, they can be sequenced and oligonucleotide probes can be prepared from sequence obtained using standard techniques. These probes can then be used to isolate DNAs encoding other forms of the DC proteins.

Oligonucleotides for use as probes are chemically synthesized according to the solid phase phosphoramidite triester method first described by Beaucage and Carruthers (1983) *Tetrahedron Lett.* 22(20):1859–1862, or using an automated synthesizer, as described in Needham-VanDevanter, et al. (1984) *Nucleic Acids Res.* 12:6159–6168. Purification of oligonucleotides is performed e.g., by native acrylamide gel electrophoresis or by anion-exchange HPLC as described in Pearson and Regnier (1983) *J. Chrom.* 255:137–149. The sequence of the synthetic oligonucleotide can be verified using the chemical degradation method of Maxam and Gilbert in Grossman, L. and Moldave (eds.) (1980) *Methods in Enzymology* 65:499–560 Academic Press, New York.

A nucleic acid encoding a human protein comprising two ubiquitin domains was isolated and sequenced. This clone has been designated A05F12 and the protein is referred to here as "diubiquitin", exhibiting two ubiquitin domains. Its nucleotide sequence and corresponding open reading frame are provided in SEQ ID NO: 1 and 2, respectively. Counterpart mouse sequence was identified, and described in SEQ ID NO: 3 and 4.

The A05F12 comprises conserved residues characteristic of a ubiquitin fold. See Monia, et al. (1990) *BioTechnology* 8:209–215. Proteins of this family have a wide range of roles in the cell, including a non-specific ligation of polypeptides and protein-protein dimerization. In particular, with regard to the human embodiment, the 165 amino acid polypeptidne could be divided into two ubiquitin-like domains, separated by 5 amino acids. The N-terminal domain, which is less highly conserved (about 29%), with respect to ubiquitin also has an initial extension of 6 amino acids. The C-terminal domain, which is more highly conserved (about 36%), contains the terminal glycine doublet which is implicated in protein-protein interactions. Lysine residues, shown by mutagenesis to be important in ubiquitin-protein binding, are conserved in both domains. See Monia, et al. (1990) *BioTechnology* 8:209–215. The two domains are more closely related to ubiquitin than to each other (about 20%), suggesting an evolution towards domains with different functions. The diubiquitin protein contains 4 cysteine residues, two in each domain, atypical of ubiquitin. See, e.g., Bates, et al. (1997) *Eur. J. Immiunol.* 27:2471–2477, which was published after the priority date of the present application.

A number of proteins are known to contain ubiquitin-like domains. A protein with two ubiquitin domains (Haas, et al. (1987) *J. Biol. Chem.* 262:11315–11323) known as the 15 kD interferon induced protein is expressed in response to interferon treatment in all cells sensitive to this treatment. The 15 kD interferon induced protein has been shown to conjugate endogenous cellular polypeptides (Loeb and Haas (1992) *J. Biol. Chem.* 267:7806–7813), and may contribute to the cellular response to viral infection. Other proteins of interest which contain ubiquitin-like domains are: NEDD-8, a mouse cDNA isolated as a neural cell protein, but present in many tissues and cell lines (Kumar, et al. (1993) Biochem. Biophys. Res. Comm. 195:393–399); RAD23A/B, proteins able to complement DNA repair in Xeroderma pigmentosum cell lines (Masutani, et al. (1994) *EMBO J.* 13:1831–1843); Bat3, a gene localized in the MHC class III complex and having a proline-rich domain preceded by a ubiquitin-like domain (Banerji, et al. (1990) *Proc. Nat'l Acad. Sci. USA* 87:2374–2378), and which may have a chaperone function; Monoclonal Non Specific Suppressor Factor beta (MNSFβ) secreted by mouse and human T cells, the product of the fau1 gene, which produces a predicted protein of 133 amino acids with a N-terminus almost identical to ubiquitin and a C terminus encoding the ribosomal protein S30 (Nakamura, et al. (1995) *Proc. Nat'l Acad. Sci. USA* 92:3463–3467), and which is cleaved into its ubiquitin-like and ribosomal parts in the cytoplasm, the former being secreted and responsible for biological activity (Nakamura, et al. (1996) *J. Immunol.* 156:533–538; GdX, which is also a ubiquitin-like N-terminal fusion gene of 157 amino acids (Toniolo, et al. (1988) *Proc. Nat'l Acad. Sci. USA* 85:851–855). In many of these proteins, the ubiquitin-like domain is essential for activity, and may be a dimerization domain for RAD23A/B, Bat3, and GdX. Diubiquitin has an N-terminal closest in homology to Rad23A/B and Bat3 and a C-terminal with greatest homology to GdX and NEDD-8. These homologies might suggest a role in dimerization for the first domain, and with the glycine terminal doublet, a role in polypeptide binding for the second domain. Genomic analysis suggests the gene is single copy, and is mapped to the HLA-F region of chromosome 6.

A second human DC clone was isolated, designated A07C03, is a member of the Ig domain superfamily of proteins. This protein is referred to herein as an Ig-family member and is described in SEQ ID NO: 5 and 6. The sequence was verified, and is disclosed in SEQ ID NO: 7 and 8. A mouse counterpart is described in SEQ ID NO: 9 and 10.

The respective Met codons for the mouse and human sequences are in a region of DNA with homology to the consensus Kozack sequence and are positioned identically on the protein sequence; significant homology between amino acids is quite striking downstream. The initiation methionines are correctly positioned with respect to the Ig-fold, leaving a short N-terminal region which may help to determine the specificity of the receptor. However, there are no stop codons immediately upstream, and only a short 3' UTR is seen upstream of the putative Met codon.

Important motifs include characteristic cysteines in the human at about residues 29 and 96, and in mouse at residues 29 and 96; a J chain region in human from about gly112 to val118 or glu121, and in mouse from about gly112 to phe154; and characteristic intracellular tyrosine residues in human at about 189 and 207, and in mouse at about 187, 191, and 204.

A third DC protein clone was isolated and designated E02B02, which is a member of the LAMP family. It is described in SEQ ID NO: 11 and 12. The message is weakly expressed in human cord blood progenitors cultured in the presence of GM-CSF and TNFα into dendritic cells, at the 6 day stage. In contrast, at days 12–16, when precursors mature into dendritic cells with typical DC morphology and phenotype, large amounts of message are detected. PCR analysis detected expression also in Lnagehans cells, but not in a population of basal cells containing mostly keratinocytes. PMA-ionomycin activated macrophages generated in vitro from CD34+ progenitors cultured with M-CSF express the message. E02B02 expression is upregulated after CD40L activation in monocyte-derived dendritic cells, as well as in CD4+CD11c+CD3-dendritic cells isolated ex vivo from tonsillar germinal centers.

This invention provides isolated DNA or fragments to encode a DC protein, as described. In addition, this invention provides isolated or recombinant DNA which encodes a biologically active protein or polypeptide which is capable of hybridizing under appropriate conditions, e.g., high stringency, with the DNA sequences described herein. Said biologically active protein or polypeptide can be a naturally occurring form, or a recombinant protein or fragment, and have an amino acid sequence as disclosed in SEQ ID NO: 2, 4, 6, 8, 10, or 12. Preferred embodiments will be full length natural isolates, e.g., from a primate or rodent. In glycosylated form, the proteins should exhibit larger sizes. Further, this invention encompasses the use of isolated or recombinant DNA, or fragments thereof, which encode proteins which are homologous to each respective DC protein. The isolated DNA can have the respective regulatory sequences in the 5' and 3' flanks, e.g., promoters, enhancers, poly-A addition signals, and others.

IV. Making DC Gene Products

DNAs which encode these DC proteins or fragments thereof can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can, e.g., be used to generate polyclonal or monoclonal antibodies; for binding studies; for construction and expression of modified molecules; and for structure/function studies. Each of these DC proteins or their fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired DC gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode the various DC proteins, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a DC protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a DC gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express DC proteins or fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and Dictyostelium, may be transformed with DC gene sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the DC protein. In principle, most any higher eukaryotic tissue culture cell line may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

In certain instances, the DC proteins need not be glycosylated to elicit biological responses in certain assays. However, it will often be desirable to express a DC polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, a DC gene may be co-transformed with one or more genes encoding mammalian or other glycosylating enzymes. It is further understood that over glycosylation may be detrimental to DC protein biological activity, and that one of skill may perform routine testing to optimize the degree of glycosylation which confers optimal biological activity.

A DC protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985) *Science* 230:1003–1008; Brunner, et al. (1991) *J. Cell Biol.* 114:1275–1283; and Coligan, et al. (eds.) (1996 and periodic supplements) *Current Protocols in Protein Science*, John Wiley & Sons, New York, N.Y.

Now that these DC proteins have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. See also Merrifield (1986) *Science* 232:341–347; and Dawson, et al. (1994) *Science* 266:776–779. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The DC proteins of this invention can be obtained in varying degrees of purity depending upon the desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and contacting the linked antibodies with solubilized lysates of appropriate source cells, lysates of other cells expressing the protein, or lysates or supernatants of cells producing the proteins as a result of DNA techniques, see below.

Multiple cell lines may be screened for one which expresses said protein at a high level compared with other cells. Various cell lines, e.g., a mouse thymic stromal cell line TA4, is screened and selected for its favorable handling properties. Natural DC cell proteins can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or $His_6$ segments can be used for such purification features.

V. Antibodies

Antibodies can be raised to the various DC proteins, including individual, polymorphic, allelic, strain, or species variants, and fragments thereof, both in their naturally occurring (full-length) forms and in their recombinant forms. Additionally, antibodies can be raised to DC proteins in either their active forms or in their inactive forms. Anti-idiotypic antibodies may also be used.

a. Antibody Production

A number of immunogens may be used to produce antibodies specifically reactive with these DC proteins. Recombinant protein is the preferred immunogen for the production of monoclonal or polyclonal antibodies. Naturally occurring protein may also be used either in pure or impure form. Synthetic peptides made using the human DC protein sequences described herein may also used as an immunogen for the production of antibodies to the DC protein. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the DC protein of interest. When appropriately high titers of antibody to the immunogen are obtained, blood is collected from the animal and antisera are prepared. Further fractionation of the antisera to enrich for antibodies reactive to the protein can be done if desired. See, e.g., Harlow and Lane.

Monoclonal antibodies may be obtained by various techniques familiar to those skilled in the art. Briefly, spleen cells from an animal immunized with a desired antigen are immortalized, commonly by fusion with a myeloma cell. See, e.g., Kohler and Milstein (1976) *Eur. J. Immunol.* 6:511–519, which is incorporated herein by reference. Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. (1989) *Science* 246:1275–1281.

Antibodies, including binding fragments and single chain versions, against predetermined fragments of these DC proteins can be raised by immunization of animals with conjugates of the fragments with carrier proteins as described above. Monoclonal antibodies are prepared from cells secreting the desired antibody. These antibodies can be screened for binding to normal or defective DC proteins, or screened for agonistic or antagonistic activity. These monoclonal antibodies will usually bind with at least a Kd of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen to initiate a humoral immune response. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029–10033.

The antibodies of this invention can also be used for affinity chromatography in isolating each DC protein. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby purified DC protein will be released.

The antibodies may also be used to screen expression libraries for particular expression products. Usually the antibodies used in such a procedure will be labeled with a moiety allowing easy detection of presence of antigen by antibody binding.

Antibodies to DC proteins may be used for the analysis or, or identification of specific cell population components which express the respective protein. By assaying the expression products of cells expressing DC proteins it is possible to diagnose disease, e.g., immune-compromised conditions, DC depleted conditions, or overproduction of DC.

Antibodies raised against each DC will also be useful to raise anti-idiotypic antibodies. These will be useful in detecting or diagnosing various immunological conditions related to expression of the respective antigens.

b. Immunoassays

A particular protein can be measured by a variety of immunoassay methods. For a review of immunological and immunoassay procedures in general, see Stites and Terr (eds.) 1991 *Basic and Clinical Immunology* (7th ed.). Moreover, the immunoassays of the present invention can be performed in any of several configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B.V., Amsterdam; and Harlow and Lane *Antibodies, A Laboratory Manual*, supra, each of which is incorporated herein by reference. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotonic Immunoassays* Plenum Press, NY.

Immunoassays for measurement of these DC proteins can be performed by a variety of methods known to those skilled in the art. In brief, immunoassays to measure the protein can be competitive or noncompetitive binding assays. In competitive binding assays, the sample to be analyzed competes with a labeled analyte for specific binding sites on a capture agent bound to a solid surface. Preferably the capture agent is an antibody specifically reactive with the DC protein produced as described above. The concentration of labeled analyte bound to the capture agent is inversely proportional to the amount of free analyte present in the sample.

In a competitive binding immunoassay, the DC protein present in the sample competes with labeled protein for binding to a specific binding agent, for example, an antibody specifically reactive with the DC protein. The binding agent may be bound to a solid surface to effect separation of bound labeled protein from the unbound labeled protein. Alternately, the competitive binding assay may be conducted in liquid phase and any of a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogenous immunoassay may be performed in which a separation step is not needed. In these immunoassays, the label on the protein is altered by the binding of the protein to its specific binding agent. This alteration in the labelled protein results in a decrease or increase in the signal emitted by label, so that measurement of the label at the end of the immunoassay allows for detection or quantitation of the protein.

These DC proteins may also be quantitatively determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of DC proteins in a sample. Electrophoresis is carried out, e.g., on a tissue sample suspected of containing the protein. Following electrophoresis to separate the proteins, and transfer of the proteins to a suitable solid support such as a nitrocellulose filter, the solid support is incubated with an antibody reactive with the denatured protein. This antibody may be labeled, or alternatively may be it may be detected by subsequent incubation with a second labeled antibody that binds the primary antibody.

The immunoassay formats described above employ labeled assay components. The label can be in a variety of forms. The label may be coupled directly or indirectly to the desired component of the assay according to methods well known in the art. A wide variety of labels may be used. The component may be labeled by any one of several methods. Traditionally a radioactive label incorporating $^3$H, $^{125}$I, $^{35}$S, $^{14}$C, or $^{32}$P is used. Non-radioactive labels include ligands which bind to labeled antibodies, fluorophores, chemiluminescent agents, enzymes, and antibodies which can serve as specific binding pair members for a labeled protein. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For reviews of immunological and immunoassay procedures applicable to the measurement of antibodies by immunoassay techniques, see, e.g., Stites and Terr (eds.) *Basic and Clinical Immunology* (7th ed.) supra; Maggio (ed.) *Enzyme Immunoassay*, supra; and Harlow and Lane *Antibodies, A Laboratory Manual*, supra.

A variety of different immunoassay formats, separation techniques, and labels can be also be used similar to those described above for the measurement of specific proteins.

VI. Purified DC proteins

The human DC diubiquitin protein amino acid sequence is provided in SEQ ID NO: 2. Mouse sequence is provided in SEQ ID NO: 4. Human nucleotide and amino acid sequences for the Ig-family member are provided in SEQ ID NO: 5, 6, 7, 8, 9, and 10. The LAMP family member from human, designated E02B02, is described in SEQ ID NO: 11 and 12. The peptide sequences allow preparation of peptides to generate antibodies to recognize such segments, and allow preparation of oligonucleotides which encode such sequences. Peptides have many other uses, e.g., to immunopurify antibodies, as agonists or antagonists of the natural forms, for structural studies, etc.

VII. Physical Variants

This invention also encompasses proteins or peptides having substantial amino acid sequence similarity with an amino acid sequence of a SEQ ID NO: 2, 4, 6, 8, 10, or 12. Variants exhibiting substitutions, e.g., 20 or fewer, preferably 10 or fewer, and more preferably 5 or fewer substitutions, are also enabled. Where the substitutions are conservative substitutions, the variants will share immunogenic or antigenic similarity or cross-reactivity with a corresponding natural sequence protein. Natural variants include individual, allelic, polymorphic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural allelic and interspecies variations in each respective protein sequence. Typical homologous proteins or peptides will have from 50–100% similarity (if gaps can be introduced), to 75–100% similarity (if conservative substitutions are included) with the amino acid sequence of the relevant DC protein. Identity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443–453; Sankoff, et al. (1983) *Time Warps, String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group (GCG), Madison, Wis.

Nucleic acids encoding the corresponding mammalian DC proteins will typically hybridize to SEQ ID NO: 1, 3, 5, 7, 9, or 11 under stringent conditions. For example, nucleic acids encoding the respective DC proteins will typically hybridize to the nucleic acid of SEQ ID NO: 1, 3, 5, 7, 9, or 11 under stringent hybridization conditions, while providing few false positive hybridization signals. Generally, stringent conditions are selected to be about 10° C. lower than the thermal melting point (Tm) for the sequence being hybridized to at a defined ionic strength and pH. The Tm is the temperature (under defined ionic strength and pH) at which 50% of the target sequence hybridizes to a perfectly matched probe. Typically, stringent conditions will be those in which the salt concentration in wash is about 0.02 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 20–50 mM NaCl at 42° C.

An isolated DC gene DNA can be readily modified by nucleotide substitutions, nucleotide deletions, nucleotide insertions, and inversions of nucleotide stretches. These modifications result in novel DNA sequences which encode these DC antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant DC protein derivatives include predetermined or site-specific mutations of the respective protein or its fragments. "Mutant DC protein" encompasses a polypeptide otherwise falling within the homology definition of the DC protein as set forth above, but having an amino acid sequence which differs from that of the DC protein as found in nature, whether by way of deletion, substitution, or insertion. In particular, "site specific mutant DC protein" generally includes proteins having significant similarity with a protein having a sequence of SEQ ID NO: 2, 4, 6, 8, 10, or 12. Generally, the variant will share many physicochemical and biological activities, e.g., antigenic or immunogenic, with those sequences, and in preferred embodiments contain most or all of the disclosed sequence. Similar concepts apply to these various DC proteins, particularly those found in various warm blooded animals, e.g., primates and mammals.

Although site specific mutation sites are predetermined, mutants need not be site specific. DC protein mutagenesis can be conducted by making amino acid insertions or deletions. Substitutions, deletions, insertions, or any combinations may be generated to arrive at a final construct. Insertions include amino- or carboxyl-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a respective DC polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, domains or other segments may be "swapped" between different new fusion polypeptides or fragments, typically with related proteins, e.g., within the Ig family or the LAMP family. Preferably, intact structural domains will be used, e.g., intact Ig portions. See, e.g., Cunningham, et al. (1989) Science 243:1330–1336; and O'Dowd, et al. (1988) J. Biol. Chem. 263:15985–15992. Thus, new chimeric polypeptides exhibiting new combinations of specificities will result from the functional linkage of protein-binding specificities and other functional domains. Also, alanine scanning mutagenesis may be applied, preferably to residues which structurally are exterior to the secondary structure, which will avoid most of the critical residues which generally disrupt tertiary structure.

"Derivatives" of these DC antigens include amino acid sequence mutants, glycosylation variants, and covalent or aggregate conjugates with other chemical moieties. Covalent derivatives can be prepared by linkage of functionalities to groups which are found in these DC protein amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents. Also, proteins comprising substitutions are encompassed, which should retain substantial immunogenicity, to produce antibodies which recognize a protein of SEQ ID NO: 2, 4, 6, 8, 10, or 12. Typically, these proteins will contain less than 20 residue substitutions from the disclosed sequence, more typically less than 10 substitutions, preferably less than 5, and more preferably less than three. Alternatively, proteins which begin and end at structural domains will usually retain antigenicity and cross immunogenicity.

A major group of derivatives are covalent conjugates of the DC proteins or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between these DC proteins and other homologous or heterologous proteins are also provided. Heterologous polypeptides may be fusions between different surface markers, resulting in, e.g., a hybrid protein. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Codowski, et al. (1988) Science 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of these DC proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a DC protein antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-DC protein antibodies. The DC proteins can also be labeled with a detectable group, e.g., radioiodinated by the chloramine T procedure, covalently bound to rare earth chelates, or conjugated to another fluorescent moiety for use in diagnostic assays. Purification of these DC proteins may be effected by immobilized antibodies.

Isolated DC protein genes will allow transformation of cells lacking expression of a corresponding DC protein, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of these DC proteins. Subcellular fragments, e.g., cytoplasts or membrane fragments, can be isolated and used.

VIII. Binding Agent:DC Protein Complexes

A DC protein that specifically binds to or that is specifically immunoreactive with an antibody generated against a defined immunogen, such as an immunogen consisting of the amino acid sequence of SEQ ID NO: 2, 4, 6, 8, 10, or 12, is determined in an immunoassay. The immunoassay uses a polyclonal antiserum which was raised to the protein of SEQ ID NO: 2, 4, 6, 8, 10, 12, or appropriate combination. This antiserum is selected to have low crossreactivity against other members of the related families, and any such crossreactivity is removed by immunoabsorption prior to use in the immunoassay. Immunoselection techniques may be used with the other members of the related family members.

In order to produce antisera for use in an immunoassay, the protein of SEQ ID NO: 2, 4, 6, 8, 10, or 12 is isolated as described herein. For example, recombinant protein may be produced in a mammalian cell line. An inbred strain of mice such as balb/c is immunized with the appropriate protein using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other related proteins, using a competitive binding immunoassay such as the one described in Harlow and Lane, supra, at pages 570–573. Preferably two different related proteins are used in this determination in conjunction with a given DC protein. For example, with the Ig family protein, at least two other family members are used to absorb out shared epitopes. In conjunction with the LAMP family member, two other members of the family are used. These other family members can be produced as recombinant proteins and isolated using standard molecular biology and protein chemistry techniques as described herein.

Immunoassays in the competitive binding format can be used for the crossreactivity determinations. For example, the protein of SEQ ID NO: 2, 4, 6, 8, 10, or 12 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2, 4, 6, 8, 10, or 12. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the DC protein of SEQ ID NO: 2, 4, 6, 8, 10, or 12). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2 that is required, then the second protein is said to specifically bind to an antibody generated to the immunogen.

It is understood that DC proteins are likely a family of homologous proteins that comprise two or more genes. For a particular gene product, such as the human Ig family member protein, the invention encompasses not only the amino acid sequences disclosed herein, but also to other proteins that are allelic, polymorphic, non-allelic, or species variants. It also understood that the term "human DC protein" includes nonnatural mutations introduced by deliberate mutation using conventional recombinant technology such as single site mutation, or by excising short sections of DNA encoding these proteins or splice variants from the gene, or by substituting or adding small numbers of new amino acids. Such minor alterations must substantially maintain the immunoidentity of the original molecule and/or its biological activity. Thus, these alterations include proteins that are specifically immunoreactive with a designated naturally occurring respective DC protein, for example, the human DC protein exhibiting SEQ ID NO: 8. Particular protein modifications considered minor would include conservative substitution of amino acids with similar chemical properties, as described above for each protein family as a whole. By aligning a protein optimally with the protein of SEQ ID NO: 2, 4, 6, 8, 10, or 12, and by using the conventional immunoassays described herein to determine immunoidentity, one can determine the protein compositions of the invention.

IX. Uses

The present invention provides reagents which will find use in diagnostic applications as described elsewhere herein, e.g., in the general description for developmental abnormalities, or below in the description of kits for diagnosis.

DC genes, e.g., DNA or RNA may be used as a component in a forensic assay. For instance, the nucleotide sequences provided may be labeled using, e.g., $^{32}$p or biotin and used to probe standard restriction fragment polymorphism blots, providing a measurable character to aid in distinguishing between individuals. Such probes may be used in well-known forensic techniques such as genetic fingerprinting. In addition, nucleotide probes made from DC sequences may be used in situ assays to detect chromosomal abnormalities.

Antibodies and other binding agents directed towards DC proteins or nucleic acids may be used to purify the corresponding DC protein molecule. As described in the Examples below, antibody purification of DC proteins is both possible and practicable. Antibodies and other binding agents may also be used in a diagnostic fashion to determine whether DC components are present in a tissue sample or cell population using well-known techniques described herein. The ability to attach a binding agent to a DC protein provides a means to diagnose disorders associated with expression misregulation. Antibodies and other DC protein binding agents may also be useful as histological markers. As described in the examples below, the expression of each of these proteins is limited to specific tissue types. By directing a probe, such as an antibody or nucleic acid to the respective DC protein, it is possible to use the probe to distinguish tissue and cell types in situ or in vitro.

This invention also provides reagents which may exhibit significant therapeutic value. The DC proteins (naturally occurring or recombinant), fragments thereof, and antibodies thereto, along with compounds identified as having binding affinity to the DC protein, may be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a DC, e.g., as an antigen presenting cell, is a target for an agonist or antagonist of the protein. The proteins likely play a role in regulation or development of hematopoietic cells, e.g., lymphoid cells, which affect immunological responses, e.g., antigen presentation and the resulting effector functions.

Other abnormal developmental conditions are known in cell types shown to possess DC protein mRNA by northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, NY. Developmental or functional abnormalities, e.g., of the immune system, cause significant medical abnormalities and conditions which may be susceptible to prevention or treatment using compositions provided herein.

Recombinant DC proteins or antibodies might be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. In particular, these may be useful in a vaccine context, where the antigen is combined with one of these therapeutic versions of agonists or antagonists. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to these DC proteins, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity might activate the cell through the protein and is thus an agonist in that it simulates the cell. This invention further contemplates the therapeutic use of antibodies to the proteins as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

The DC proteins, fragments thereof, and antibodies to it or its fragments, antagonists, and agonists, could be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, N.Y.; Lieberman, et al. (eds.) (1990) *Pharmaceutical Dosaae Forms: Tablets* Dekker, N.Y.; and Lieberman, et al. (eds.) (1990) *Pharmaceutical Dosage Forms: Disperse Systems* Dekker, N.Y. The therapy of this invention may be combined with or used in association with other chemotherapeutic or chemopreventive agents.

Both the naturally occurring and the recombinant form of the DC proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, e.g., soluble versions of, DC protein as provided by this invention.

For example, antagonists can often be found once the protein has been structurally defined. Testing of potential protein analogs is now possible upon the development of highly automated assay methods using a purified surface protein. In particular, new agonists and antagonists will be discovered by using screening techniques described herein. Of particular importance are compounds found to have a combined binding affinity for multiple related cell surface antigens, e.g., compounds which can serve as antagonists for species variants of a DC protein.

This invention is particularly useful for screening compounds by using recombinant DC protein in a variety of drug screening techniques. The advantages of using a recombinant protein in screening for specific ligands include: (a) improved renewable source of the protein from a specific source; (b) potentially greater number of antigens per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a DC protein. Cells may be isolated which express that protein in isolation from any others. Such cells, either in viable or fixed form, can be used for standard surface protein binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of DC protein) are contacted and incubated with an antibody having known binding affinity to the antigen, such as $^{125}$I-antibody, and a test sample whose binding affinity to the binding composition is being measured. The bound and free labeled binding compositions are then separated to assess the degree of protein binding. The amount of test compound bound is inversely proportional to the amount of labeled antibody binding to the known source. Many techniques can be used to separate bound from free reagent to assess the degree of binding. This separation step could typically involve a procedure such as adhesion to filters followed by washing, adhesion to plastic followed by washing, or centrifugation of the cell membranes. Viable cells could also be used to screen for the effects of drugs on these DC protein mediated functions, e.g., antigen presentation or helper function.

Another method utilizes membranes from transformed eukaryotic or prokaryotic host cells as the source of a DC protein. These cells are stably transformed with DNA vectors directing the expression of the appropriate protein, e.g., an engineered membrane bound form. Essentially, the membranes would be prepared from the cells and used in binding assays such as the competitive assay set forth above.

Still another approach is to use solubilized, unpurified or solubilized, purified DC protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to the respective DC protein and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified DC protein, and washed. The next step involves detecting bound reagent, e.g., antibody.

One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

X. Kits

This invention also contemplates use of these DC proteins, fragments thereof, peptides, and their fusion products in a variety of diagnostic kits and methods for detecting the presence of a DC protein or message. Typically the kit will have a compartment containing either a defined DC peptide or gene segment or a reagent which recognizes one or the other, e.g., antibodies.

A kit for determining the binding affinity of a test compound to the respective DC protein would typically comprise a test compound; a labeled compound, for example an antibody having known binding affinity for the protein; a source of the DC protein (naturally occurring or recombinant); and a means for separating bound from free labeled compound, such as a solid phase for immobilizing the DC protein. Once compounds are screened, those having suitable binding affinity to the protein can be evaluated in suitable biological assays, as are well known in the art, to determine whether they act as agonists or antagonists to regulate DC function. The availability of recombinant DC polypeptides also provide well defined standards for calibrating such assays.

A preferred kit for determining the concentration of, for example, a DC protein in a sample would typically comprise a labeled compound, e.g., antibody, having known binding affinity for the DC protein, a source of DC protein (naturally occurring or recombinant) and a means for separating the bound from free labeled compound, for example, a solid phase for immobilizing the DC protein. Compartments containing reagents, and instructions, will normally be provided.

Antibodies, including antigen binding fragments, specific for the respective DC or its fragments are useful in diagnostic applications to detect the presence of elevated levels of the protein and/or its fragments. Such diagnostic assays can employ lysates, live cells, fixed cells, immunofluorescence, cell cultures, body fluids, and further can involve the detection of antigens in serum, or the like. Diagnostic assays may be homogeneous (without a separation step between free reagent and antigen-DC protein complex) or heterogeneous (with a separation step). Various commercial assays exist, such as radioimmunoassay (RIA), enzyme-linked immunosorbentassay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to the DC protein or to a particular fragment thereof. Similar assays have also been extensively discussed in the literature. See, e.g., Harlow and Lane (1988) *Antibodies: A Laboratory Manual*, CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY. In particular, the reagents may be useful for diagnosing DC populations in biological samples, either to detect an excess or deficiency of DC in a sample. The assay may be directed to histological analysis of a biopsy, or evaluation of DC numbers in a blood or tissue sample.

Anti-idiotypic antibodies may have similar use to diagnose presence of antibodies against a DC protein, as such may be diagnostic of various abnormal states. For example, overproduction of the DC protein may result in various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or receptor, or labeled DC protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification or may be modified in a variety of ways. For example, labeling may be achieved by covalently or non-covalently joining a moiety which directly or indirectly provides a detectable signal. In many of these assays, the protein, test compound, DC protein, or antibodies thereto can be labeled either directly or indirectly. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free protein, or alternatively the bound from the free test compound. The DC protein can be immobilized on various matrices followed by washing. Suitable matrices include plastic such as an ELISA plate, filters, and beads. Methods of immobilizing the DC protein to a matrix include, without limitation, direct adhesion to plastic, use of a capture antibody, chemical coupling, and biotin-avidin. The last step in this approach involves the precipitation of protein/antibody complex by one of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a respective DC protein. These sequences can be used as probes for detecting levels of the message in samples from patients suspected of having an abnormal condition, e.g., cancer or immune problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

XI. Binding Partner Isolation

Having isolated one member of a binding partner of a specific interaction, methods exist for isolating the counter-partner. See, Gearing, et al. (1989) *EMBO J.* 8:3667–3676. For example, means to label a DC surface protein without interfering with the binding to its receptor can be determined. For example, an affinity label can be fused to either the amino- or carboxyl-terminus of the ligand. An expression library can be screened for specific binding to the DC protein, e.g., by cell sorting, or other screening to detect subpopulations which express such a binding component. See, e.g., Ho, et al. (1993) *Proc. Nat'l Acad. Sci. USA* 90:11267–11271. Alternatively, a panning method may be used. See, e.g., Seed and Aruffo (1987) *Proc. Nat'l Acad. Sci. USA* 84:3365–3369. A two-hybrid selection system may also be applied making appropriate constructs with the available DC protein sequences. See, e.g., Fields and Song (1989) *Nature* 340:245–246.

Protein cross-linking techniques with label can be applied to isolate binding partners of a DC protein. This would allow identification of proteins which specifically interact with the appropriate DC protein.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY.

Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1996 and periodic Supplements) *Current Protocols in Protein Science* Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Encineering, Principle and Methods* 12:87–98, Plenum Press, NY; and Crowe, et al. (1992) *OIAexpress: The High Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991) *Current Protocols in Immunology* Wiley/Greene, NY; and *Methods in Enzymology* volumes 70, 73, 74, 84, 92, 93, 108, 116, 121, 132, 150, 162, and 163. Methods for determining immunological function are described, e.g., in Coligan, et al. (1992 and periodic Supplements) *Current Protocols in Immunology* Wiley/Greene, NY. See also, e.g., Paul (ed.) (1993) *Fundamental Inmmunology* (3d ed.) Raven Press, N.Y.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Generation of dendritic cells

Human CD34+ cells were obtained as follows. See, e.g., Caux, et al. (1995) pages 1–5 in Banchereau and Schmitt *Dendritic Cells in Fundamental and Clinical Immunology* Plenum Press, NY. Peripheral or cord blood cells, sometimes CD34+ selected, were cultured in the presence of Stem Cell Factor (SCF), GM-CSF, and TNF-α in endotoxin free RPMI 1640 medium (GIBCO, Grand Island, N.Y.) supplemented with 10% (v/v) heat-inactivated fetal bovine serum (FBS; Flow Laboratories, Irvine, Calif.), 10 mM HEPES, 2 mM L-glutamine, $5\times10^{-5}$ M 2-mercaptoethanol, penicillin (100 μg/ml). This is referred to as complete medium.

CD34+ cells were seeded for expansion in 25 to 75 cm² flasks (Corning, N.Y.) at $2\times10^4$ cells/ml. Optimal conditions were maintained by splitting these cultures at day 5 and 10 with medium containing fresh GM-CSF and TNF-α (cell concentration: $1-3\times10^5$ cells/ml). In certain cases, cells were FACS sorted for CD1a expression at about day 6.

In certain situations, cells were routinely collected after 12 days of culture, eventually adherent cells were recovered using a 5 mM EDTA solution. In other situations, the CD1a+ cells were activated by resuspension in complete medium at $5\times10^6$ cells/ml and activated for the appropriate time (e.g., 1 or 6 h) with 1 μg/ml phorbol 12-myristate 13-acetate (PMA, Sigma) and 100 ng/ml ionomycin (Calbiochem, La Jolla, Calif.). These cells were expanded for another 6 days, and RNA isolated for cDNA library preparation.

III. RNA isolation and library construction

Total RNA is isolated using, e.g., the guanidine thiocyanate/CsCl gradient procedure as described by Chirgwin, et al. (1978) *Biochem.* 18:5294–5299.

Alternatively, poly(A)+ RNA is isolated using the OLIGOTEX mRNA isolation kit (QIAGEN). Double stranded cDNA are generated using, e.g., the SUPERSCRIPT plasmid system (Gibco BRL, Gaithersburg, Md.) for cDNA synthesis and plasmid cloning. The resulting double stranded cDNA is unidirectionally cloned, e.g., into pSport1 and transfected by electroporation into ELECTROMAX DH10BTM Cells (Gibco BRL, Gaithersburg, Md.).

Mouse or other species sources may also be used.

IV. Sequencing

DNA isolated from randomly picked clones, or after subtractive hybridization using unactivated cells, were subjected to nucleotide sequence analysis using standard techniques. A Taq DiDeoxy Terminator cycle sequencing kit (Applied Biosystems, Foster City, Calif.) can be used. The labeled DNA fragments are separated using a DNA sequencing gel of an appropriate automated sequencer. Alternatively, the isolated clone is sequenced as described, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1–3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Chemical sequencing methods are also available, e.g., using Maxam and Gilbert sequencing techniques.

V. Isolation of human DC protein genes

The A05F12, the A07C03, and E02B02 clones were sequenced, and analyzed for open reading frames. The clones were further analyzed to extend the nucleic acid sequence to a full, or nearly full, open reading frame.

mRNA is prepared from appropriate cell populations by the FastTrack kit (Invitrogen) from which cDNA is generated using, e.g., SuperScript Plasmid System for cDNA synthesis from GIBCO-BRL (Gathersburg, Md.) essentially as described by the manufacturer. Modification to the procedure may include the substitution of other cloning adapters for the Sal1 adapters provided with the kit. The resultant cDNA from these cells is used to generate libraries, e.g., in the plasmid PcDNA II (Invitrogen). The cDNA is cloned into the polylinker and is used to transform an appropriate strain, e.g., DH10B, of E. coli. Plasmid is isolated and purified, e.g., with the Qiagen system (Chatsworth, Calif.) which is used to generate RNA probes from, e.g., the SP6 promoter.

RNA probes are labeled, e.g., using the Genius System (Boehringer-Mannheim) as described by the manufacturer. Filter lifts of the cDNA library can be pre-hybridized, e.g., at 42° C. for 3–6 hours in Church's buffer (50% formamide, 6×SSPE, 50 mM $NaHPO_4$ pH7.2, 7% SDS, 0.1% N-Lauryl sarcosine, 2% Boehringer-Mannheim blocking reagent). Filters are probed, e.g., overnight in the same buffer containing the appropriate probes. The filters are washed, e.g., as described by the Genius System. The colonies that hybridize are selected.

The entire cDNA of human DC proteins are sequenced, e.g., by the dideoxynucleotide chain termination method with T7 polymerase (U.S. Biochemicals, Cleveland, Ohio) using double-stranded DNA as template. Data base searching and sequence analysis are performed using IntelliGenetics programs (Mountain View, Calif.) to determine if homology exists between previously reported clones.

Table 1 discloses sequence encoding a human diubiquitin protein, which contains two ubiquitin domains which extend from about 1 (met) to about 83 (pro) and from about 89 (pro) to about 165 (gly). The putative polypeptide sequence comprises four cysteine residues which are not characteristic of a human ubiquitin domain. Related proteins are reported in, e.g., Nrasimhan, et al. (1996) *J. Biol. Chem.* 271:324–330; Lowe, et al. (1995) *J. Pathology* 177:163–169; Loeb and Haas (1994) *Mol. and Cell. Biol.* 14:8408–8419; Loeb and Haas (1992) *J. Biol. Chem.* 267:7806–7813. The diubiquitin protein also exhibits similarity to the monoclonal non-specific suppressor factor beta (MNSFb) produced by mouse and human T cells. The MNSFb is a protein of about 133 residues with an N-terminus similar to ubiquitin and a C-terminus similar to the S30 ribosomal protein. The MNSFb protein is cleaved into two portions in the cytoplasm, the ubiquitin-like domain is secreted. The MNSFb is reported to inhibit the generation of LPS-induced immunoglobulin secreting cells, the proliferation of mitogen-activated T and B cells, the IL-4 secretion by bone marrow derived mast cells, and the growth of various murine tumor cell lines. See Nadamura, et al. (1995) *Proc. Nat'l Acad. Sci. USA* 92:3463–3467; Nakamura, et al. (1996) *J. Immunol.* 156:532–538; Nakamura, et al. (1995) *Eur. J. Immunol.* 25:2417–2419; Xavier, et al. (1995) *Immunobiology* 192:262–271; Xavier, et al. (1994) *J. Immunol.* 152:2624–2632; and others.

Note that the ubiquitin conserved residues 48 (lys) and 70 (lys) are present here, which residues have been implicated in protein binding. The terminal glycine doublet is also characteristic of the proteins. This sequence was isolated from an activated CD1a dendritic cell library, and exhibits substantial identity with EST sequence U37231 and a pig SSCE11. The first Met is downstream from a Kozak consensus sequence suggesting that it may be the initiation codon.

Ubiquitination may play a role in the generation of the MHC class I binding epitope in antigen presentation.

This suggests that the protein may play a role in the DC function of antigen presentation. The gene seems to be a single copy gene, and exhibits no homologs when a low stringency Southern hybridization is performed. PCR analysis indicates that the message is present at high levels in dendritic cells; at lower levels in JY (B cell line); at even lower levels in CHA (carcinoma cell line); and not detected in TF1 (hematopoietic cell line), Jurkat (T cell line), MRC5 (lung fibroblast sarcoma cell line), or U937 (pre-monocyte cell line). On Northern analysis, a single band of 0.9 kb was seen in dendritic cells, but was less intense with JY cells, and not detected in the other cell lines tested by PCR. In a more physiological analysis, the levels were very low to undetectable in fresh T cells, granulocytes, B cells, and monocytes. Thus, the protein is a useful marker for quantitating or distinguishing dendritic cells from these other cell types. The analysis may be destructive of the cells. Tissue distribution in fetal tissue message blots showed no detectable presence in brain, lung, liver, and kidney, but no positive control was present. Similarly, in adult tissues: heart, brain, placenta, lung, liver, skeletal muscle, kidney, pancreas, spleen, thymus, prostate, testis, ovary, small intestine, colon, or PBL, though there is no positive tissue control in the sample.

The A07C03 sequence encoding a protein related to Ig family members was also isolated from an activated CD1a dendritic cell library. At about positions 578 and 710, various isolates have various insertions/deletions which suggest positions of intron splicing. A putative hydrophobic stretch or signal sequence may run from about 1 (met) to about 22 (val), and a potential transmembrane segment runs from about 154 (phe) to about 176 (leu). This suggests that the protein is a membrane protein, and may well be a receptor for another cel surface molecule in an interacting cell. Certain cysteine residues, e.g., at positions 51 and 118 are characteristic of Ig domains. A region similar to the J chain of a type 1 variable chain runs from about 134 (gly) to about 141 (val). Two putative glycosylation sites are found in the part amino proximal to the transmembrane portion, with various putative phosphorylation sites in the carboxy proximal part.

Sequence analysis suggests A07C03 is a member of the Ig superfamily of receptors, and is closely related to the CD8 family, which members contain a V1J-type fold. The prediction of size and start of protein is based, in part, upon those sequence comparisons. The analysis also includes secondary sequence structural analysis. A mouse counterpart is probably encoded in the EST W55567, isolated from brain. The sequence exhibits some homology with the R95734 sequence, and low similarity with a number of immunoglobulin V chain regions, particularly with the domain 2 of the polymeric immunoglobulin receptor (pIgR) The pIgR is expressed in a wide variety of cell types, including epithelial and neuronal cells, and is transcytosed toward the cell membrane in a specific manner and binds to and internalizes polymeric immunoglobulins, particularly di-IgA. A soluble form, secretory component, is implicated in the secretion of immunoglobulins. See, e.g., Cardone and Mostov (1995) *FEBS Lett.* 376:74–76; Nihei, et al. (1995) *Arch. Dermatolog. Res.* 287:546–552; de Hoop, et al. (1995) *J. Biol. Chem.* 130:1447–1459; Ferkol, et al. (1995) *J. Clin. Invest.* 95:493–502; and Mazanec, et al. (1995) *J. Virol.* 69:1339–1343.

The CD8 family members are typically dimers, and the T cells receptors are quasi-homodimers. These receptors typically bind to heterophillic ligands, and the A07C03 is likely to bind to a molecule on an interacting cell type, e.g., a T or B cell, or other cell type found in the germinal centers where the dendritic cells perform critical roles in the initiation and control of immune responses.

RT-PCR provides a strong signal only in dendritic cells. Northern blot analysis gives a single band at about 1 kb in activated or resting DC and monocytes, but no detectable signal is seen in activated T cells, granulocytes, resting or activated PBL, or B cells. No detectable signal is seen in TF1 (hematopoietic cell line), Jurkat (T cell line), CHA (carcinoma cell line), MRC5 (lung fibroblast sarcoma cell line), JY (B cell line), or U937 (pre-monocyte cell line). In adult tissues, two messages of about 1 and 2.5 kb are seen in spleen and PBMC, but not in heart, brain, placenta, lung, liver, skeletal muscle, kidney, pancreas, thymus, prostate, testis, ovary, small intestine, or colon.

A sequence encoding a protein related to LAMP-like family members, designated E02B02, was isolated from human CD1a dendritic cells. The initiation methionine is not found in this clone, but sequence analysis suggests that it is not far upstream of the sequence provided. The encoded protein exhibits homology to Lysosome-Associated Membrane Protein (LAMP) family, see human lysosomal LMP1 (P11279) and LMP2 (P49130) and CD68 (P34810). Notable features are a hydrophobic length from about −23 (met) to about −1 (ser), putatively a signal sequence; a likely transmembrane segment from about ile359 to leu383; and a serine/proline rich stretch suggestive of a hinge from about pro184 to ser199. Residues arg384 to ile392 are a cytoplasmic tail.

Northern blot analysis gives a single band at about 3.5 kb in resting or activated DC, but no detectable signal is seen in monocytes, activated T cells, granulocytes, resting or activated PBL, or B cells. A strong positive signal is seen in dendritic cells and a weak signal in Jurkat (T cell line), but no detectable signal is seen in TF1 (hematopoietic cell line), CHA (carcinoma cell line), MRC5 (lung fibroblast sarcoma cell line), JY (B cell line), or U937 (pre-monocyte cell line). In adult tissues, a message of about 3.5 kb is seen in liver, but not in heart, brain, placenta, lung, skeletal muscle, kidney, pancreas, spleen, thymus, prostate, testis, ovary, small intestine, colon, or PBL. Tissue distribution in fetal tissue message blots showed no detectable presence in brain, lung, liver, and kidney, but no positive control was present.

The E02B02 message is weakly expressed in human cord blood progenitors cultured in the presence of GM-CSF and TNFα into dendritic cells, at the 6 day stage. In contrast, at days 12–16, when precursors mature into dendritic cells with typical DC morphology and phenotype, large amounts of message are detected. PCR analysis detected expression also in Langerhans cells, but not in a population of basal cells containing mostly keratinocytes. PMA-ionomycin activated macrophages generated in vitro from CD34+ progenitors cultured with M-CSF express the message. E02B02 expression is upregulated after CD40L activation in monocyte-derived dendritic cells, as well as in CD4+ CD11c+CD3-dendritic cells isolated ex vivo from tonsillar germinal centers.

FACS analysis reveals that DC-LAMP expression increases during DC maturation. It thus represents a useful marker for mature dendritic cells. On tonsil sections, DC-LAMP stains specifically interdigitating DC in the T cell area, but not in the germinal center. Thus, the CD-LAMP is a useful specific marker for interdigitating DC.

Confocal microscopy suggests that this DC-LAMP may specifically stain a novel lysosomal compartment. In comparison with the LAMP-1 and LAMP-2 proteins and Class II on CD34+ derived DC, the DC-LAMP stains different lysosomes, possibly the same ones involved in the transport of MHC-Class II complexes.

The lysosomal protein homology suggests that this protein may be involved in that compartment in the DC, and possibly related to degradation of protein in antigen presentation functions.

VI. Recombinant DC gene construct

Poly(A)$^+$ RNA is isolated from appropriate cell populations, e.g., using the FastTrack mRNA kit (Invitrogen, San Diego, Calif.). Samples are electrophoresed, e.g., in a 1% agarose gel containing formaldehyde and transferred to a GeneScreen membrane (NEN Research Products, Boston, Mass.). Hybridization is performed, e.g., at 65° C. in 0.5 M NaHPO$_4$ pH 7.2, 7% SDS, 1 mM EDTA, and 1% BSA (fraction V) with $^{32}$P-dCTP labeled DC gene cDNA at $10^7$ cpm/ml. After hybridization filters are washed three times at 50° C. in 0.2×SSC, 0.1% SDS, and exposed to film for 24 h.

The recombinant gene construct may be used to generate probe for detecting the message. The insert may be excised and used in the detection methods described above.

VII. Expression of DC gene Protein in *E. coli.*

PCR is used to make a construct comprising the open reading frame, preferably in operable association with proper promoter, selection, and regulatory sequences. The resulting expression plasmid is transformed into an appropriate, e.g., the Topp5, *E. coli* strain (Stratagene, La Jolla, Calif.). Ampicillin resistant (50 μg/ml) transformants are grown in Luria Broth (Gibco) at 37° C. until the optical density at 550 nm is 0.7. Recombinant protein is induced with 0.4 mM isopropyl-βD-thiogalactopyranoside (Sigma, St. Louis, Mo.) and incubation of the cells continued at 20° C. for a further 18 hours. Cells from a 1 liter culture are harvested by centrifugation and resuspended, e.g., in 200 ml of ice cold 30% sucrose, 50 mM Tris HCl pH 8.0, 1 mM ethylenediaminetetraacetic acid. After 10 min. on ice, ice cold water is added to a total volume of 2 liters. After 20 min. on ice, cells are removed by centrifugation and the supernatant is clarified by filtration via a 5 μM Millipak 60 (Millipore Corp., Bedford, Mass.).

The recombinant protein is purified via standard purification methods, e.g., various ion exchange chromatography methods. Immunoaffinity methods using antibodies described below can also be used. Affinity methods may be used where an epitope tag is engineered into an expression construct.

VIII. Mapping of human DC genes

DNA isolation, restriction enzyme digestion, agarose gel electrophoresis, Southern blot transfer and hybridization are performed according to standard techniques. See Jenkins, et al. (1982) *J. Virol.* 43:26–36. Blots may be prepared with Hybond-N nylon membrane (Amersham). The probe is labeled with $^{32}$P-dCTP; washing is done to a final stringency, e.g., of 0.1×SSC, 0.1% SDS, 65° C.

Alternatively, a BIOS Laboratories (New Haven, Conn.) mouse somatic cell hybrid panel may be combined with PCR methods. The diubiquitin gene matches the EST U37231, which maps to the MHC Class I region, e.g., human chromosome 6. See Fan, et al. (1996) *Immunogenetics* 44:97–103.

The E02B02 gene has been mapped to human chromosome 3, bands 3q26.3-q27. This is a different chromosomal localization than the LAMP-1 and LAMP-2 genes.

IX. Analysis of individual variation

From the distribution data, an abundant easily accessible cell type is selected for sampling from individuals. Using PCR techniques, a large population of individuals are analyzed for this gene. cDNA or other PCR methods are used to sequence the corresponding gene in the different individuals, and their sequences are compared. This indicates both the extent of divergence among racial or other populations, as well as determining which residues are likely to be modifiable without dramatic effects on function.

X. Preparation of Antibodies

Recombinant DC proteins are generated by expression in *E. coli* as shown above, and tested for biological activity. Active or denatured proteins may be used for immunization of appropriate mammals for either polyclonal serum production, or for monoclonal antibody production.

XI. Isolation of counterpart primate or rodent DC genes

Human cDNA clones encoding these genes are used as probes, or to design PCR primers to find counterparts in various primate species, e.g., chimpanzees. Likewise, mouse sequences may be used to isolate counterpart sequences from other rodent species.

XII. Use of reagents to analyze cell populations

Detection of the level of dendritic cells present in a sample is important for diagnosis of aberrant disease conditions. For example, an increase in the number of dendritic cells in a tissue or the lymph system can be indicative of the presence of a DC hyperplasia, or tissue or graft rejection. A low DC population can indicate an abnormal reaction to, e.g., a bacterial or viral infection, which may require the appropriate treat to normalize the DC response.

FACS analysis using a labeled binding agent specific for a cell surface DC protein, see, e.g., Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y., is used in determining the number of DCs present in a cell mixture, e.g., PBMCs, adherent cells, etc. The binding agent is also used for histological analysis of tissue samples, either fresh or fixed, to analyze infiltration of DC. Diverse cell populations may also be evaluated, either in a cell destructive assay, or in certain assays where cells retain viability.

Analysis of the presence of soluble intracellular molecules is performed, e.g., with a fluorescent binding agent specific for a DC as described in Openshaw, et al. (1995) *J. Exo. Med*. 182:1357–1367. alternatively, tissue or cell fixation methods may be used.

Levels of DC transcripts are quantitated, e.g., using semiquantitative PCR as described in Murphy, et al. (1993) *J. Immunol. Methods* 162:211–223. Primers are designed such that genomic DNA is not detected.

XIII. Isolation of a binding counterpart

A DC protein can be used as a specific binding reagent, by taking advantage of its specificity of binding, much like an antibody would be used. A binding reagent is either labeled as described above, e.g., fluorescence or otherwise, or immobilized to a substrate for panning methods.

The DC protein is used to screen for a cell line which exhibits binding. Standard staining techniques are used to detect or sort intracellular or surface expressed ligand, or surface expressing transformed cells are screened by panning. Screening of intracellular expression is performed by various staining or immunofluorescence procedures. See also McMahan, et al. (1991) *EMBO J*. 10:2821–2832.

For example, on day 0, precoat 2-chamber permanox slides with 1 ml per chamber of fibronectin, 10 ng/ml in PBS, for 30 min. at room temperature. Rinse once with PBS. Then plate COS cells at $2–3 \times 10^5$ cells per chamber in 1.5 ml of growth media. Incubate overnight at 37° C.

On day 1 for each sample, prepare 0.5 ml of a solution of 66 mg/ml DEAE-dextran, 66 mM chloroquine, and 4 mg DNA in serum free DME. For each set, a positive control is prepared, e.g., of human receptor-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin(0.1%) with 32 ml/ml of 1M $NaN_3$ for 20 min. Cells are then washed with HBSS/saponin 1×. Add protein or protein/antibody complex to cells and incubate for 30 min. Wash cells twice with HBSS/saponin. If appropriate, add first antibody for 30 min. Add second antibody, e.g., Vector anti-mouse antibody, at 1/200 dilution, and incubate for 30 min. Prepare ELISA solution, e.g., Vector Elite ABC horseradish peroxidase solution, and pre-incubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min., which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min. at 85–90° C.

Alternatively, other DC protein specific binding reagents are used to affinity purify or sort out cells expressing a receptor. See, e.g., Sambrook, et al. or Ausubel, et al.

Another strategy is to screen for a membrane bound receptor by panning. The receptor cDNA is constructed as described above. The ligand can be immobilized and used to immobilize expressing cells. Immobilization may be achieved by use of appropriate antibodies which recognize, e.g., a FLAG sequence of a DC protein fusion construct, or by use of antibodies raised against the first antibodies. Recursive cycles of selection and amplification lead to enrichment of appropriate clones and eventual isolation of ligand expressing clones.

Phage expression libraries can be screened by DC protein. Appropriate label techniques, e.g., anti-FLAG antibodies, will allow specific labeling of appropriate clones.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

SEQUENCE SUBMISSION

SEQ ID NO: 1 is human A05F12 diubiquitin nucleotide sequence.
SEQ ID NO: 2 is human A05F12 diubiquitin polypeptide sequence.
SEQ ID NO: 3 is mouse A05F12 diubiquitin nucleotide sequence.
SEQ ID NO: 4 is mouse A05F12 diubiquitin polypeptide sequence.
SEQ ID NO: 5 is human A07C03 Ig family gene nucleotide sequence.
SEQ ID NO: 6 is human A07C03 Ig family gene polypeptide sequence.
SEQ ID NO: 7 is revised human A07C03 Ig family gene nucleotide sequence.
SEQ ID NO: 8 is revised human A07C03 Ig family gene polypeptide sequence.
SEQ ID NO: 9 is mouse A07C03 Ig family gene nucleotide sequence.
SEQ ID NO: 10 is mouse A07C03 Ig family gene polypeptide sequence.
SEQ ID NO: 11 is human E02B02 LAMP-like gene nucleotide sequence.
SEQ ID NO: 12 is human E02B02 LAMP-like gene polypeptide sequence.

What is claimed is:

1. An isolated or recombinant polynucleotide encoding a polypeptide comprising the amino acid sequence of SEQ ID NO:2 or SEQ ID NO:4.

2. The isolated or recombinant polynucleotide of claim 1, wherein said isolated or recombinant polynucleotide comprises SEQ ID NO:3.

3. The isolated or recombinant polynucleotide of claim 1, wherein said isolated or recombinant polynucleotide is:

a) attached to a solid substrate;
b) detectably labeled;
c) in a sterile composition; or
d) synthetically produced.

4. An expression vector comprising the isolated or recombinant polynucleotide of claim 1.

5. A host cell comprising the expression vector of claim 4.

6. A method of producing a polypeptide of SEQ ID NO:2 or SEQ ID NO:4 comprising:

a) culturing the host cell of claim 5 under conditions suitable for expression of said polypeptide; and b) isolating the polypeptide from the culture.

7. A kit comprising:

a) said isolated or recombinant polynucleotide of claim 1; and b) instructions for use or disposal of reagents in said kit.

8. An isolated or recombinant polynucleotide encoding at least a polypeptide comprising SEQ ID NO:12 or an antigenic polypeptide thereof.

9. The isolated or recombinant polynucleotide of claim 8, wherein said isolated or recombinant polynucleotide encodes a polypeptide of SEQ ID NO:12.

10. The isolated or recombinant polynucleotide of claim 8, wherein said isolated or recombinant polynucleotide comprises SEQ ID NO:11.

11. The isolated or recombinant polynucleotide of claim 8, wherein said isolated or recombinant polynucleotide is:

a) attached to a solid substrate;

b) detectably labeled;

c) in a sterile composition; or d) synthetically produced.

12. An expression vector comprising the isolated or recombinant polynucleotide of claim 8.

13. A host cell comprising the expression vector of claim 12.

14. A method of producing a polypeptide of SEQ ID NO:2 or SEQ ID NO:4 comprising:

a) culturing the host cell of claim 13 under conditions suitable for expression of said polypeptide; and b) isolating the polypeptide from the culture.

15. A kit comprising:

a) said isolated or recombinant polynucleotide of claim 8; and b) instructions for use or disposal of reagents in said kit.

16. The isolated or recombinant polynucleotide of claim 8, wherein said polynucleotide is from a human.

* * * * *